United States Patent [19]
Starr

[11] 4,261,041
[45] Apr. 7, 1981

[54] METHOD AND APPARATUS FOR CONTROLLING A MICROPROCESSOR-BASED SYSTEM

[75] Inventor: Gilbert Starr, New Rochelle, N.Y.
[73] Assignee: Medtek Corporation, Princeton, N.J.
[21] Appl. No.: 64,195
[22] Filed: Aug. 6, 1979
[51] Int. Cl.³ .............................................. G06F 15/20
[52] U.S. Cl. .................... 364/571; 364/579; 364/580; 364/900
[58] Field of Search ............... 364/571, 579–580, 364/119, 900, 200, 107

[56] References Cited

U.S. PATENT DOCUMENTS

| | | | |
|---|---|---|---|
| 3,764,995 | 10/1973 | Helf, Jr. et al. | 364/579 X |
| 4,043,756 | 8/1977 | Sommervold | 364/571 X |
| 4,155,116 | 5/1979 | Tawfik et al. | 364/579 X |
| 4,168,527 | 9/1979 | Winkler | 364/580 |

Primary Examiner—Edward J. Wise
Attorney, Agent, or Firm—Gottlieb, Rackman & Reisman

[57] ABSTRACT

There is disclosed a microprocessor-based system whose firmware controls a normal mode of operation and a factory-adjustment mode of operation. The sequencing in the two modes is controlled by branching in accordance with system-state tests performed during the sequencing. The factory-adjustment mode of operation never takes place during normal use of the system, and a branch to the factory-adjustment mode is controlled by forcing particular system-state test signals in the factory. Where no extra test pins are available, a branch to the factory-adjustment mode can be controlled by forcing two incompatible test signals, that is, by forcing an overall system state which cannot occur during normal operation.

24 Claims, 11 Drawing Figures

FIG. 9   8 ACdEFHILoOPrSUY

FIG. 6
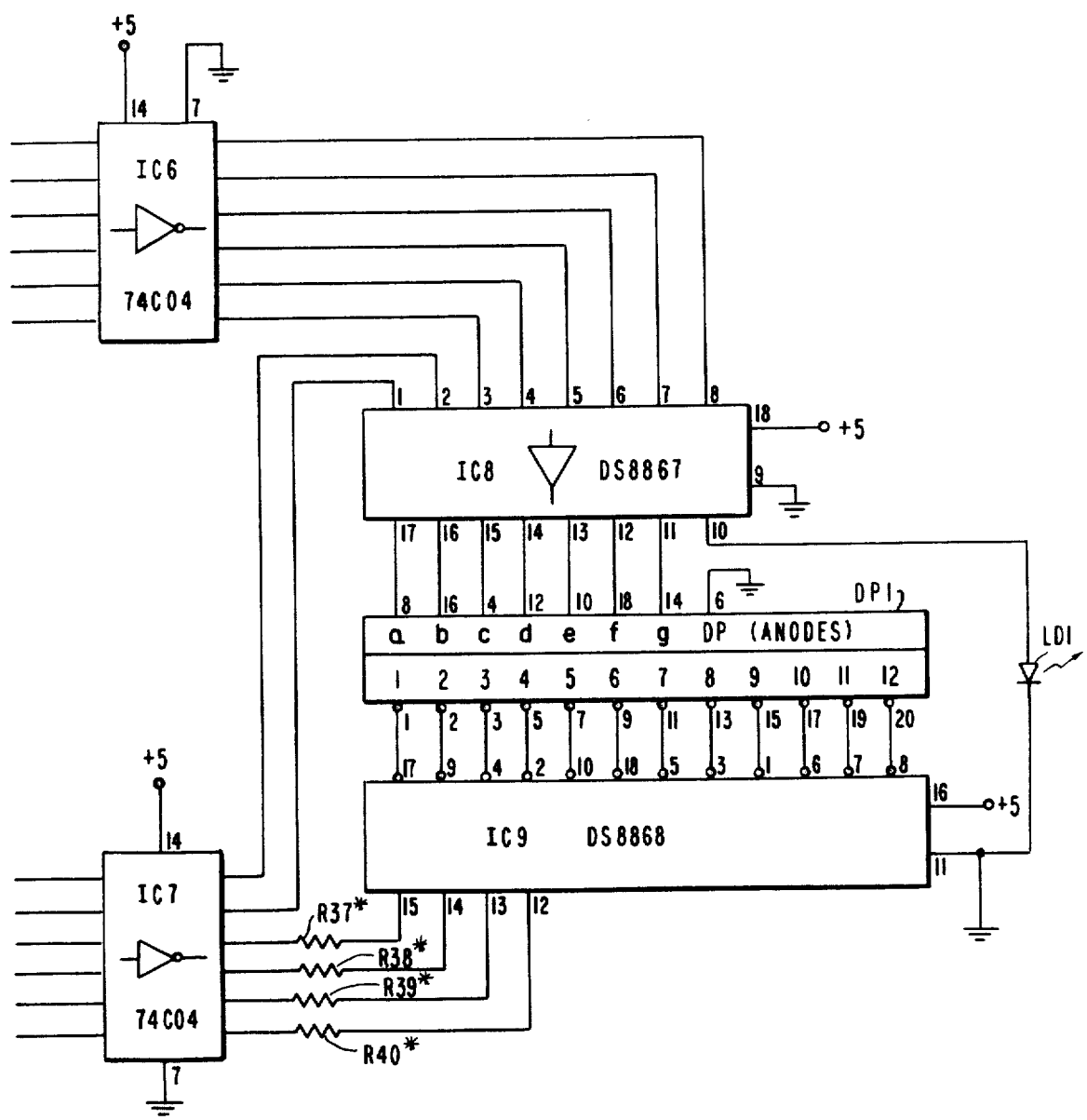
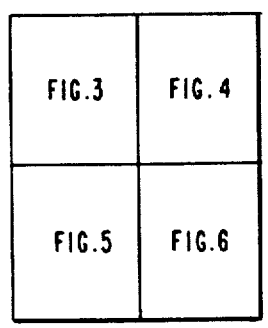
FIG. 7

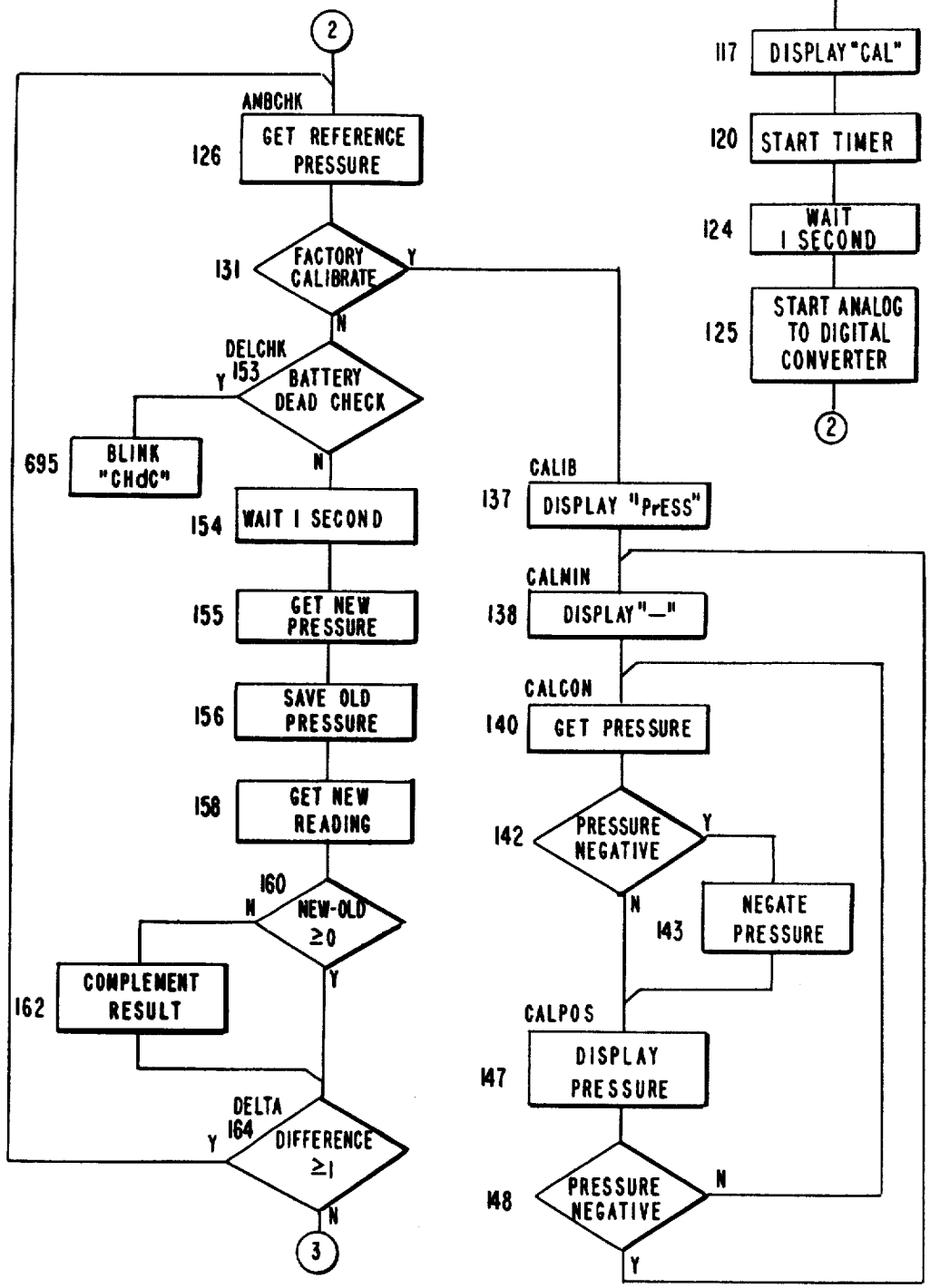

METHOD AND APPARATUS FOR CONTROLLING A MICROPROCESSOR-BASED SYSTEM

This invention relates to microprocessor-based systems, and more particularly to a method and means for controlling sequencing in two different modes.

In many microprocessor-based systems whose sequencing is controlled by a series of "instructions" coded in firmware (either on the microprocessor chip, or on a separate chip), there often comes a point at which the system must choose between two different modes of operation. This is usually accomplished by testing an external condition, or test signal or signals (representing the system state), and controlling a branch depending upon the result of the test.

But there are situations in which the choice of sequencing in one of two modes is not necessarily dependent on a naturally occurring system state. For example, consider an instrument which, once sold to a customer, always operates in what may be called a "normal" mode (the intended end use), but which may have to be operated in another mode in the factory. One such instrument might be designed, inter alia, to measure and display the value of some parameter of interest, e.g., pressure. When operated in the normal mode, the system sequence may entail taking a measurement and then controlling an appropriate display, with the display being constantly up-dated as the pressure changes. Such an instrument usually includes potentiometers or other components which can be adjusted for calibration purposes. During calibration, a known pressure may be measured by the instrument, and potentiometers adjusted until the correct pressure value is displayed. The instrument sequences in a "factory-adjustment" mode which is different from the way it sequences when operated in the normal mode (even though portions of the two different sequences may be the same, e.g., the actual steps in driving the display). The sequencing in the factory-adjustment mode is usually controlled to a significant degree by manual operations of a technician.

It is a general object of my invention to provide a system in which a minimum amount of external control is required to sequence an instrument in a factory-adjustment mode.

Many microprocessor-based systems include firmware for controlling self-testing. For example, many instruments perform a test sequence when they are first turned on; they test their own operations to verify that they are in working order before they commence to operate for their intended purpose. The firmware code for controlling these tests is of the same type as the firmware code for controlling the normal sequencing because the self-testing is part of the normal sequencing. The "factory-adjustment" mode with which the invention is concerned entails a sequence of steps which is not performed while the system is in the hands of the end user. (By the term "factory", I include a sequence performed in a service center, or even at the user site. The "factory-adjustment" mode, as used herein, is a mode of operation which is not routinely executed, is not a part of the normal functioning of the apparatus, and instead is employed only occasionally for special repair or calibration purposes. It is a mode of operation which facilitates the making of changes in the system which then affect operation in the normal mode.)

The usual way in which a system is operated in a factory-adjustment mode is for a technician to control the sequencing manually, invariably by doing more than simply operating a single switch. But in accordance with the principles of my invention, the sequencing in the factory-adjustment mode is controlled by a separate portion of the firmware which is included in the unit. This firmware is not executed during normal use of the apparatus; it is used only when the apparatus is to be adjusted. Despite the fact that once the system is shipped it may never have to be "factory-adjusted" again, the firmware included in the unit includes code for controlling this type of sequencing. The advantage of simplifying the steps required of a technician in the factory to adjust the device, by having the device automatically cycle in the proper manner, more than outweighs the disadvantage of "wasting" some of the firmware capacity by storing code which may never be used after the unit is shipped.

The question arises how to control the choice of normal and factory-adjustment modes of operation. The easiest way to do this is to utilize a test signal. The test signal is normally at one level; when the unit is used by the ultimate consumer, the test signal is always in this state. The firmware controls an examination of the test signal, and controls a branch to that portion of the firmware which controls sequencing in the normal mode. Only when the system is to be operated in the factory-adjustment mode does a technician physically force the test signal to the opposite state, for example, by connecting it to battery or ground—the state which is opposite to that in which the test signal is always maintained after the unit is shipped. When the firmware controls an examination of the test signal which is now in the forced state, a branch is made to that portion of the firmware which controls sequencing in the factory-adjustment mode.

While in theory this approach is fine, in designing "real" systems it would appear that the technique would often be impractical. A microprocessor has a limited number of pins for communicating with the external world. Most of these pins are used for transmitting data, address and control signals. There are usually only a limited number of pins left over for inputting test signals. (The test signal inputs may take many forms—separate pins provided for this purpose, particular bit positions of an input port, or even the interrupt control pin.) In fact, one of the biggest problems in the design of new and more powerful microprocessors is the requirement for a greater number of pins. For example, recent microprocessors have the capability of addressing a very large address space, and this requires a wide address bus. Similarly, a 16-bit microprocessor may require a 16-bit data bus rather than the 8-bit data bus in less powerful designs. There is a limit to the number of pins which can actually be included with a chip, and in most cases there are only a limited number of pins to which test signals can be applied. What will often happen in practice, when trying to design a system in which sequencing in either the normal or factory-adjustment mode is controlled by a forced test signal, is that one will find no pins left over to which the test signal can be applied. In such a case, there is no apparent way to provide a test signal to which the microprocessor has access for controlling sequencing in one of the two modes.

My solution to this problem is predicated on the realization that many of the test signals which are examined during a normal mode of operation can only assume predetermined combinations. In other words, there are usually certain combinations of incompatible test conditions. By utilizing the same test inputs which are used during the normal mode of operation, but by having the technician force at least two of the test signals to represent incompatible test conditions, the microprocessor may be informed that sequencing in the factory-adjustment mode is required and an appropriate branch in the firmware taken. The incompatible test conditions can never arise during normal operation; they can only arise when they are forced by a technician in the factory.

In the illustrative embodiment of the invention, the apparatus is battery-powered and two test inputs are utilized for examining the battery potential. Each test input is a 0 if the battery potential is below a respective level, and it is a 1 if the battery potential is above the respective level. The two levels in the illustrative embodiment of the invention are 9.4 volts and 9.8 volts. If the battery potential exceeds 9.8 volts, no message is displayed to the user indicative of the state of the battery. If the battery potential is between 9.4 and 9.8 volts, the instrument can still be used, but the operator is informed to re-charge the batteries. If the battery potential is below 9.4 volts, the operator is informed by an appropriate message that the instrument cannot be used (because to do so would lead to inaccurate results). Two test inputs are required because the microprocessor cannot test the actual magnitude of an input; it is only capable of distinguishing between high and low levels (0 and 1). Accordingly, analog circuitry determines whether the battery potential exceeds 9.8 volts, and if it does a high level (1) is applied to the 9.8-volt test input. Similarly, analog circuitry determines whether the battery potential exceeds 9.4 volts, and if it does a high level (1) is applied to the 9.4-volt test input.

When the instrument is used in the normal mode, there are three possible combinations for the two test inputs. If they are both 1, it is an indication that the battery potential exceeds 9.8 volts. If they are both 0, it is an indication that the battery potential is less than 9.4 volts. If the 9.4-volt test input is a 1 and the 9.8-volt test input is a 0, it is an indication that the battery potential is between 9.4 and 9.8 volts. The "impossible" combination is a 0 for the 9.4-volt test input and a 1 for the 9.8-volt test input—this would indicate that the battery potential is greater than 9.8 volts and at the same time less than 9.4 volts. This condition can obviously never arise when the instrument is used in the normal mode. But a technician may force "incompatible" test conditions in the factory simply by using a jumper to connect an appropriate point in the analog circuitry to battery or ground. In the factory, if a new battery is used and tested separately, it is known that it is greater than 9.8 volts and, accordingly, the 9.8-volt test input will be a 1. All the technician has to do is to force the 9.4-volt test input to be a 0 even though it would otherwise be a 1 due to the fully charged state of the battery. The microprocessor examines the two test inputs (or system state), and when it detects the incompatible test conditions it causes a branch to the firmware which controls sequencing in the factory-adjustment mode. After adjustment, the jumper is removed and the unit shipped to the consumer. Thereafter, the "impossible" combination of test inputs never arises, and the system never sequences in the factory-adjustment mode.

This technique effectively allows a branch to be controlled without requiring any additional test inputs. Even though all available test inputs are used for other purposes during normal sequencing, an additional state condition can actually be determined.

The illustrative embodiment of my invention is employed in a blood pressure measuring instrument. The instrument is disclosed in the patent application of Michael Croslin, entitled "Method and Apparatus for Performing Non-Invasive Blood Pressure and Pulse Rate Measurements", filed on even date herewith and assigned to the assignee of this application, which Croslin application is hereby incorporated by reference. Only that part of the Croslin disclosure which pertains to my invention will be described herein. The details of taking blood pressure measurements are not essential for an understanding of the present invention. The drawing included herewith comprises only a portion of the Croslin drawing—that portion required for an understanding of the present invention.

Further objects, features and advantages of my invention will become apparent upon consideration of the following detailed description in conjunction with the drawing (which is identical to the same-numbered figures in the Croslin application), in which:

FIGS. 3-6 are a schematic of the circuit of the instrument, with the figures being arranged as shown in FIG. 7;

FIG. 9 depicts the seven segments of each display element, together with the fifteen characters which can be formed by energizing appropriate ones of the segments (the 16th character is a blank, obtained by energizing none of the segments); and FIGS. 10 and 11 are flow charts depicting that part of the overall instrument operation which comprises the illustrative embodiment of my invention.

In the illustrative blood pressure measuring instrument, a display is provided for guiding the operator—physician or patient—through the measurement cycle. As a conventional bulb is used to pump up the cuff pressure, the operator is informed not only of the instantaneous cuff pressure, but also of the particular actions which are required. Instantaneous cuff pressures are measured at 2.5-millisecond intervals by using a pressure transducer which is in open communication with the cuff. For a measurement cycle to provide accurate results, it is essential that the artery be completely occluded before the cuff pressure is monitored for the presence of pulses. The system checks that no pulses have been detected for about 2.5 seconds before it assumes that the artery has been completely occluded and the cuff pressure should be allowed to continue bleeding down. If full occlusion for 2.5 seconds is not ascertained, the display informs the operator to pump up the cuff pressure.

The basic systolic pressure methodology involves an analysis of the amplitudes of four successive pulses, when pulses first appear as the occluding pressure bleeds down. (Artifacts are rejected and it is not necessarily the first four pulse amplitudes which are operated upon.) Systolic pressure is taken to be the cuff pressure at the onset of a particular one of the four pulses, but only if the pulse amplitudes have a sequence which is one of a plurality of known valid sequences, e.g., four successive pulses exhibit increasing amplitudes, except for the third which may have the largest amplitude. There are quite a few valid sequences, as described in the Croslin application.

The diastolic pressure methodology involves the determination of a threshold value based upon maximum pulse amplitude information; the threshold level is a function of both a constant and the maximum average pulse amplitude over four pulses. When the average pulse amplitude over four pulses falls below the threshold value, diastolic pressure is established.

Throughout the processing, validation checks are performed. Any indication of erroneous measurements having been taken results in an appropriate error message. Accurate measurements of pulse rates are also provided. In connection with a pulse rate measurement, while it is not particularly difficult to count detected pulses, it is the rejection of a measurement cycle due to the presence of artifacts that gives rise to the high accuracy of the Croslin methodology.

Hardware

Figure 1:
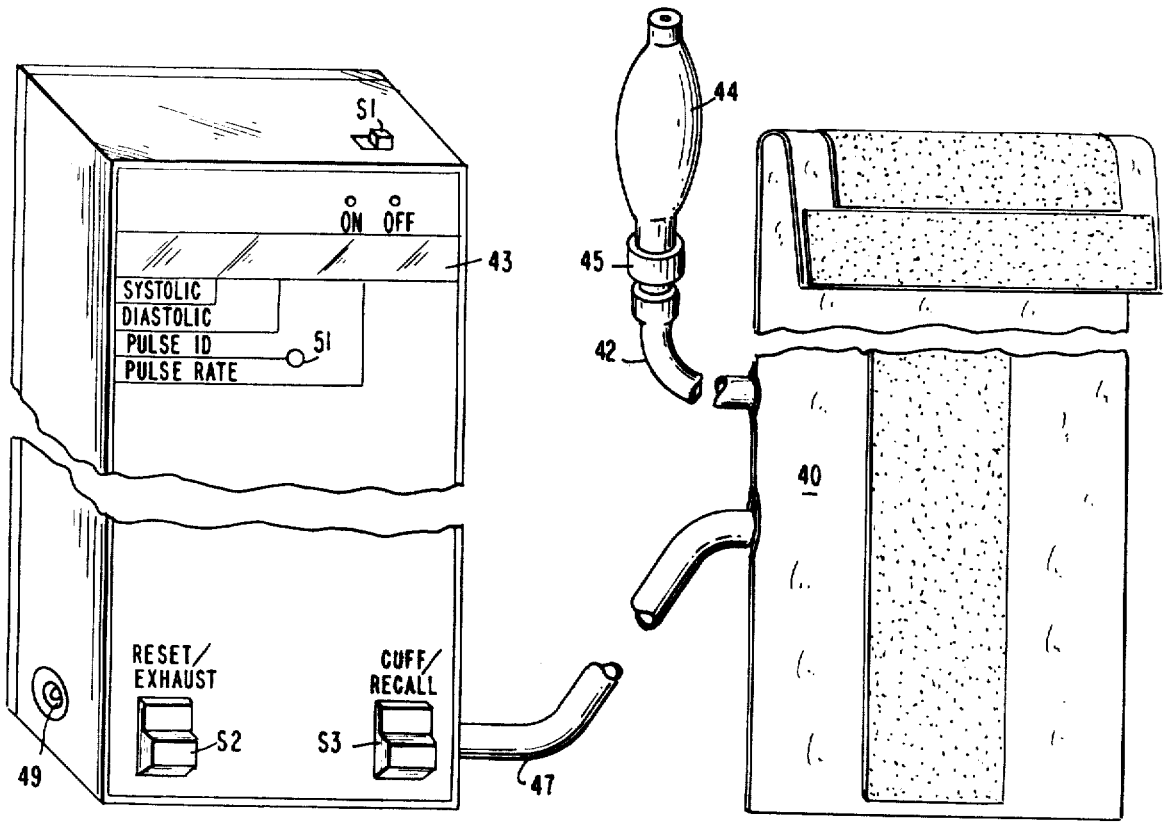
FIG. 1 is a perspective view of a blood pressure measuring instrument.

FIG. 1 depicts the instrument in which the illustrative embodiment of my invention is employed. It includes a conventional cuff 40, with tubing 42 connecting the cuff to pump-up bulb 44. As the bulb is pumped, the pressure in the cuff rises. There is a bleed valve 45 in the bulb which allows air in the cuff to bleed out at a rate of several mm Hg per second, the actual bleed rate depending upon the cuff pressure. Tubing 47 connects the cuff to a manifold within the instrument housing. The overall cuff arrangement is standard except that the take-off tubing 47 is extended to the instrument rather than to a mercury column as in conventional blood pressure measuring instruments.

The instrument itself includes three switches and a twelve-character display DP1 (under a red translucent strip 43). Switch S1 (on the top) is the main on/off switch which, when operated, connects the internal batteries to the circuit. (The unit also includes a jack 49 for insertion of the plug of a charging circuit when it is necessary to recharge the batteries.) Switch S2 is the reset/exhaust switch which is spring-loaded to an open position. When it is momentarily closed, the instrument resets and initiates a new cycle of operation. Switch S3, another normally-open, spring-loaded push-button, is the recall/cuff control. When it is operated, one of two different sequences takes place depending upon the state of the instrument at the time the button is operated. Toward the beginning of the overall cycle, operation of switch S3 closes take-off tubing 47 so that the pressure in the cuff can be pumped up by repeatedly squeezing bulb 44. At the end of a measurement cycle, the final values are displayed for only ten seconds, and the display is then blanked to converve power. Operation of switch S3 causes the previously determined values to be displayed once again, for another ten seconds.

The display itself consists of 12 character positions, each of which has seven light-emitting diode segments as shown at the left of FIG. 9. Depending upon which of the segments are energized, any one of 15 characters can be displayed at each position, the 15 characters also being shown in FIG. 9 and it being obvious which of the seven segments are used to form each of the fifteen characters. A blank may be displayed simply by energizing no segments. The display elements are also used to form numerals as is well known in the art.

The instrument also includes a light-emitting diode LD1 (under a red translucent area 51 on the case) which, when illuminated, represents one of two things. First, the light is on whenever the system is in the process of detecting a blood pressure pulse (a rise in the occluding cuff pressure). Second, after the final display has been blanked in order to conserve power, the light is turned on to indicate to the operator that the display can be recalled if switch S3 is momentarily operated. Lastly, the positions on the display of the final measurement values are printed on the case.

Figure 2:
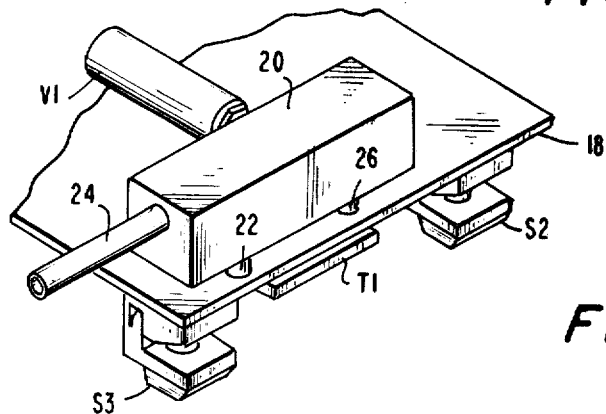
FIG. 2 depicts a portion of the circuit board within the housing of the instrument, and several of the components mounted on the board.

FIG. 2 depicts just one part of the circuit board 18 on which the circuit components are mounted within the housing. Switch S3 can be seen in the drawing. In addition, a manifold 20 is mounted on the board, and spaced from it by spacer 22. The manifold provides open communication between input pipe 24 (on which take-off tubing 47 of FIG. 1 is placed), a pipe segment 26, and a valve V1. The valve is normally open, but when its two leads (not shown) have a potential applied across them, the valve closes. A pressure transducer T1 is mounted on the other side of the board—the side on which all of the chips used in the circuit are mounted—and the input port of the transducer is connected to pipe segment 26. It is apparent that since pipe 24 is connected via take-off tubing 47 to the cuff, transducer T1 has as its "input" the cuff pressure. Valve V1 is used to open the cuff to the atmosphere, within and through the housing, so that the cuff pressure can rapidly decrease at the end of a measurement cycle. The valve is closed automatically by the circuit after switch S3 is operated so that the pump-up procedure can commence. It is important to note that transducer T1 is located within the instrument housing and is not positioned in the cuff (although it could be). Thus there are no circuit elements which are in contact with the patient.

The schematic of the circuit is shown in FIGS. 3–6. Many of the chips are identified on the schematic, and the omitted chip identifications, as well as the component values, are as follows (many of the resistors are contained in four resistor networks, identified by the symbols RA1-RA4, which will be discussed below):

| C1 | 22uf | C26 | .1uf |
|---|---|---|---|
| C2 | .01uf | C27 | .1uf |
| C3 | 6.8uf | R1* | 18.7K (RA2) |
| C4 | 6.8uf | R2* | 19.6K (RA2) |
| C5 | .01uf | R3* | 1M (RA2) |
| C6 | .47uf | R4* | 10K (RA2) |
| C7 | .01uf | R5* | 18.7K (RA2) |
| C8 | .01uf | R6* | 1M (RA2) |
| C9 | 22uf | R7* | 10K (RA2) |
| C10 | .01uf | R8* | 21.5K (RA2) |
| C11 | .47uf | R9 | 1K |
| C12 | .01uf | R10* | 20K (RA2) |
| C13 | .47uf | R11* | 100K (RA2) |
| C14 | .01uf | R12* | 20K (RA2) |
| C15 | 10f | R13* | 5.6K (RA1) |
| C16 | 22uf | R14* | 100K (RA2) |
| C17 | .47uf | R15* | 330 (RA4) |
| C19 | 1uf | R16* | 20K (RA1) |
| C20 | 1uf | R17* | 4.7K (RA3) |
| C21 | .01uf | R18* | 15K (Ra1) |
| C22 | 270pf | R19 | 10K |
| C23 | 68pf | R20 | 2K |
| C24 | 20pf | R21* | 20K (RA1) |
| C25 | 20pf | R22 | 1K |
| R23* | 5K (RA2) | Ra1 | Custom 16-Pin Dip, 1% |
| R24 | 100 | RA2 | Custon 16-Pin Dip, 1% |
| R25* | 10K (RA1) | RA3 | Bourns 4310R-102-472 (10-Pin Sip), 1% |
| R26 | 100 | | |
| | | RA4 | Bourns 4310R-102-331 |

| | | | |
|---|---|---|---|
| R27* | 7.5K (RA1) | | (10-Pin Sip), 1% |
| R28* | 402K (RA1) | | |
| | | D1 | IN4001 |
| R29* | 10K (RA1) | | |
| | | D2 | IN4001 |
| R30* | 330 (RA4) | | |
| | | D6 | IN4001 |
| R31* | 10K (RA1) | | |
| | | Z1 | IN5523 |
| R32* | 330 (RA4) | | |
| | | IC3 | LM324 |
| R33* | 330 (RA4) | | |
| | | IC10 | LM393N |
| R34* | 330 (RA4) | | |
| | | IC11 | DS88L12N |
| R35* | 162K (RA1) | | |
| | | LD1 | RL209-2 |
| R36* | 40.2K (RA1) | | |
| | | V1 | Angar Scientific |
| R37* | 4.7K (RA3) | | Controls, Model |
| | | | 336073 (East Hanover, |
| R38* | 4.7K (RA3) | | New Jersey) |
| R39* | 4.7K (RA3) | DP1 | NSA7120 |
| R40* | 4.7K (RA3) | | |
| R41 | 47 (1/2W) | | |

Figure 3:
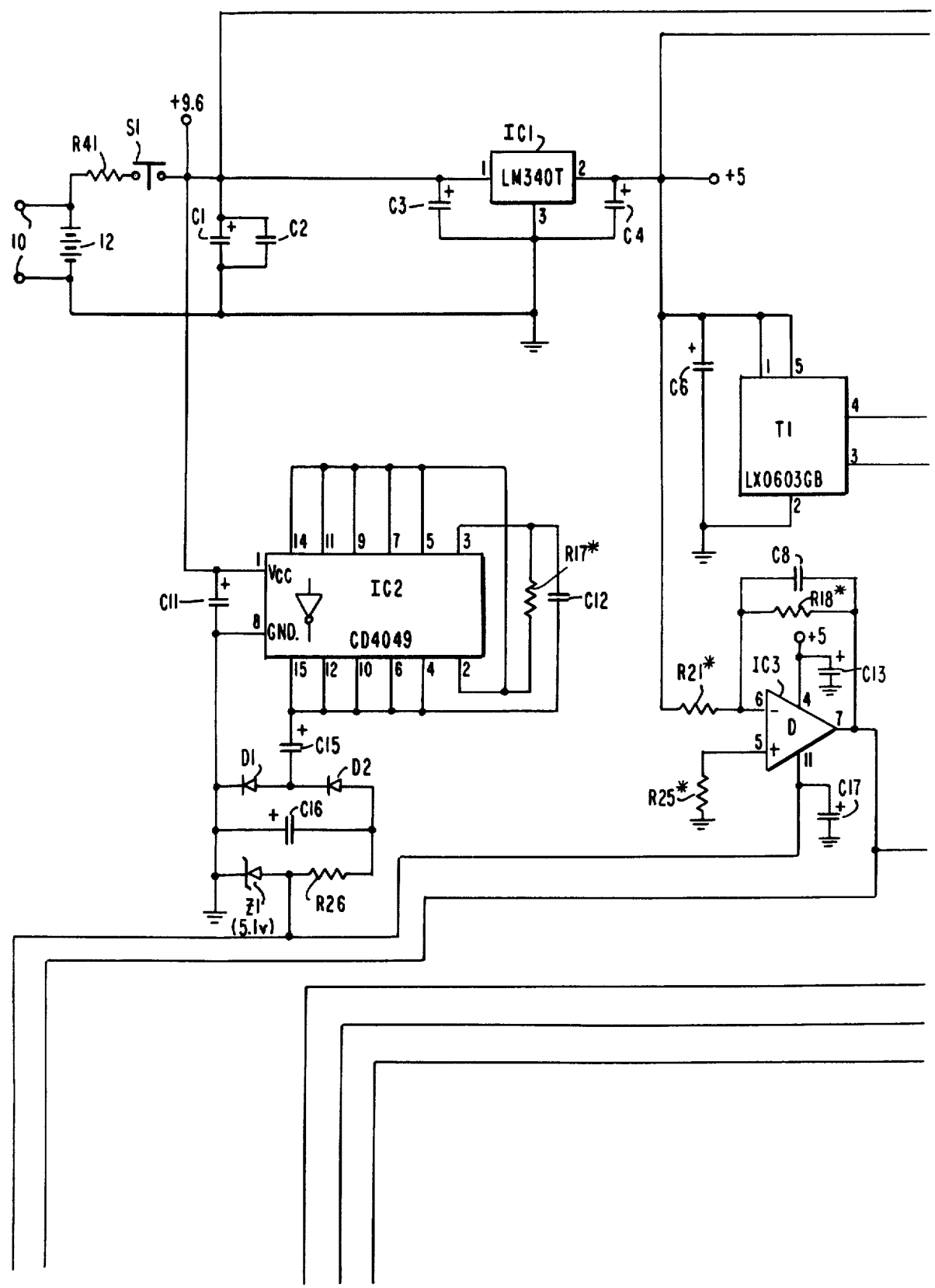

In FIG. 3, the numeral 12 depicts eight 1.4-volt batteries. Although each battery has a nominal voltage of 1.4 volts, the system is designed to operate even if the overall voltage falls as low as 9.4 volts. Terminals 10 simply depict the points at which a charging circuit may be connected to the instrument to recharge the batteries. When switch S1 is closed, power is furnished to the circuit. A potential of 9.6 volts is shown to the right of switch S1, since this is a typical actual potential in normal use. Chip IC1 is a voltage regulator which derives a 5-volt regulated potential at its output pin 2. The circuitry directly below switch S1 and chip IC1 is a standard circuit for deriving a −5.1-volt potential at the junction of Zener diode Z1 and resistor R26. This negative potential is required for proper operation of chip IC4. Chip IC2 is arranged as a 10-kHz oscillator. The configuration is standard, and five of the six inverters on the chip are connected in parallel to lower the output impedance so that charge can be dumped faster into capacitor C16. The circuit is shown on page 1–50 of the "Data Conversion Design Manual" published by Teledyne Semiconductor, 1979.

Transducer T1 on FIG. 3 is a National Semiconductor chip—a pressure transducer utilizing a piezoresistive circuit which derives an output voltage across pins 3 and 4 which is proportional to applied pressure. It is the pressure port of the transducer (not shown in FIG. 3) which is coupled to pipe segment 26 in FIG. 2. Amplifier D of chip IC3 on FIG. 3, and the associated components, are used to develop a −3.75-volt reference voltage which is applied through resistor R27 (FIG. 4) to the positive input of amplifier A of chip IC3.

Many of the resistors are marked in the schematic with asterisks. These asterisks identify the resistors as being included in one of four resistor networks, as will be described below in connection with FIG. 8.

Figure 4:
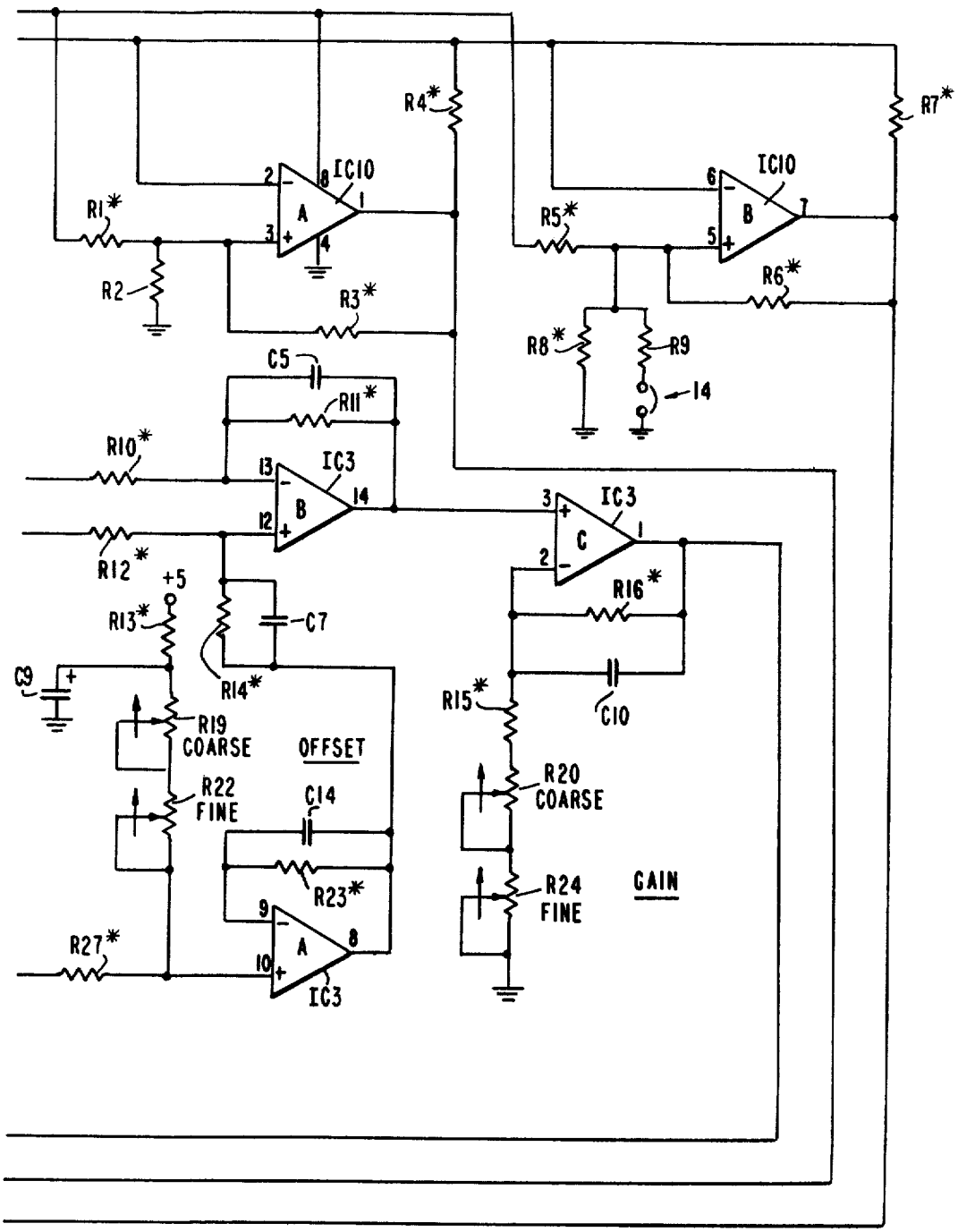

The ambient output of transducer T1 may range between +50-mv and −50-mv. The analog-to-digital converter chip IC4 (FIG. 5) works on positive inputs only, and thus an offset is introduced by amplifier A of chip IC3 (FIG. 4). The amplifier itself is used in a unity gain configuration, and the coarse and fine potentiometer controls R19 and R22 are used to provide an ambient potential difference across pins 12 and 13 of differential amplifier B of chip IC3 which is in the 30-mv to 50-mv range. The output at pin 14 of amplifier B of chip IC3 is extended to the positive input of amplifier C of the same chip. This is the gain amplifier which is provided with coarse and fine potentiometer controls R20 and R24. The potential at pin 1 of chip IC3 is extended to the analog input at pin 14 of chip IC4, the analog-to-digital converter. It is this chip, on FIG. 5, which derives samples of the instantaneous cuff pressure, as reflected by the analog output at pin 1 of chip IC3.

The ambient output when the cuff pressure is open to the atmosphere need not be precise. In fact, it varies with temperature and atmospheric pressure. The system self-calibrates itself by deriving a reference pressure at the output of the analog-to-digital converter when the cuff is at atmospheric pressure. Thus at the start of any measurement cycle, the analog signal furnished to the converter is non-zero, but this is of no moment because the system subtracts the reference pressure from each actual sample taken. Thus all sample values which are processed by the apparatus are pressures which are relative to atmospheric pressure.

In the factory, however, the offset and gain potentiometers are adjusted to provide accurate readings. Tubing 42 in FIG. 1 is connected to a pump-up bulb without a bleed hole and to an accurate mercury manometer. If the cuff is initially at atmospheric pressure, the instrument should read a pressure of zero, since each sample, less the reference atmospheric pressure, should provide a value of zero. During the factory-calibrate mode, the instrument actually displays the cuff pressure as will be described below. The operator manipulates the two offset potentiometers until a pressure reading of zero is obtained. Thereafter, the bulb is pumped up. Since a bleed hole is not provided in the bulb, the pressure in the cuff remains constant at the pumped-up value. The instrument may display a pressure value which is different from the actual value as represented on the manometer. The two gain potentiometers are adjusted until the pressure reading (relative to the reference pressure) displayed by the instrument is correct. By thus manipulating both pairs of potentiometers, the instrument can be calibrated in the factory. Thereafter, it is the use of the reference pressure subtraction technique which insures that all displayed pressures are pressures which are relative to atmospheric pressure, so that temperature and altitude considerations are of little importance.

Comparators A and B of chip IC10 on FIG. 4 serve to develop two test signals. The output of comparator A is high whenever the battery potential, connected to the positive input, is greater than 9.8 volts. The output of comparator B is high whenever the battery potential exceeds 9.4 volts. The two signals at the outputs of the comparators are used in two different ways.

During normal processing, as will be described below, the "test" signals at the outputs of the two comparators are used to inform the system of the state of the battery. If both test signals are high, indicating a battery potential greater than 9.8 volts, the system provides no "state-of-the-battery" message to the operator. But if the output of amplifier B is high and the output of amplifier A is low, it is an indication that the battery potential exceeds 9.4 volts but does exceed 9.8 volts. In such a case, the instrument is capable of performing up to 25 more measurements so it continues to function. However, the operator is provided with a message indicating that the batteries should be recharged. If both test signals are low, the system will not allow measurements to be taken, and a message is displayed which informs the operator that the batteries must be recharged before the instrument can be used.

It will be noted that pin 5 of chip IC10 is connected through resistor R8 (21.5K) to ground. Resistor R9 (1k) is in parallel with it, but this resistor is left floating. In the factory, a test clip, symbolized by the numeral 14, can be used to ground the lower end of resistor R9. By so doing, the output of comparator B is forced low. A factory technician does this when the unit is to be calibrated.

The system includes a microprocessor and firmware for controlling its cycling. (The Intel 8048 chip which is used includes the firmware together with the microprocessor on the same chip, although other microprocessors with separate ROM chips can be employed.) The firmware includes instructions for cycling the system in the factory-calibrate mode; these instructions are not actually accessed during normal use of the instrument, and control cycling of the machine only in the factory-calibrate mode. During the factory-calibrate procedure, all the system does is to measure cuff pressure and to display it so that the operator may manipulate the potentiometer controls. The instructions for cycling in the factory-calibrate mode are included in the firmware which is shipped in the unit despite the fact that, after factory calibration, this part of the firmware is not used (unless re-calibration is ever required, in which case the unit may be thought of as being calibrated in the "factory"). The system therefore must have a way of knowing whether it is to cycle in the normal mode or in the factory-calibrate mode. It is jumper 14 which does this.

When a unit is being calibrated in the factory, fresh batteries are in it and thus the output of comparator A of chip IC10 is high, indicating that the battery potential is above 9.8 volts. But when resistor R9 is connected to ground by the jumper, the output of comparator B of chip IC10 is forced low, indicating that the battery potential is below 9.4 volts. The two test conditions are thus inconsistent with each other, since they indicate battery potentials which are both above and below and intermediate level. When the system detects these inconsistent test conditions, it branches to the factory-calibrate mode of operation.

The advantage of this technique is that it allows a branch to be controlled in the firmware without the need for another test input to the microprocessor. As will become apparent below, all of the pins of the 8048 microprocessor are utilized, and there is no available pin which can be used as a separate test input. Were such a pin available, it would be relatively simple to apply an appropriate potential to it in the factory which would cause a branch to the factory-calibrate mode of operation. But in the absence of an available pin, it would appear that there is no way for the microprocessor to test whether it should branch to the factory-calibrate mode of operation. But since two battery test signals are required anyway, an effective state test can be controlled by forcing the two battery test signals to represent inconsistent conditions. Such inconsistent signals never arise during the normal mode of operation, since the battery potential can never be both above and below an intermediate level.

Figure 5:
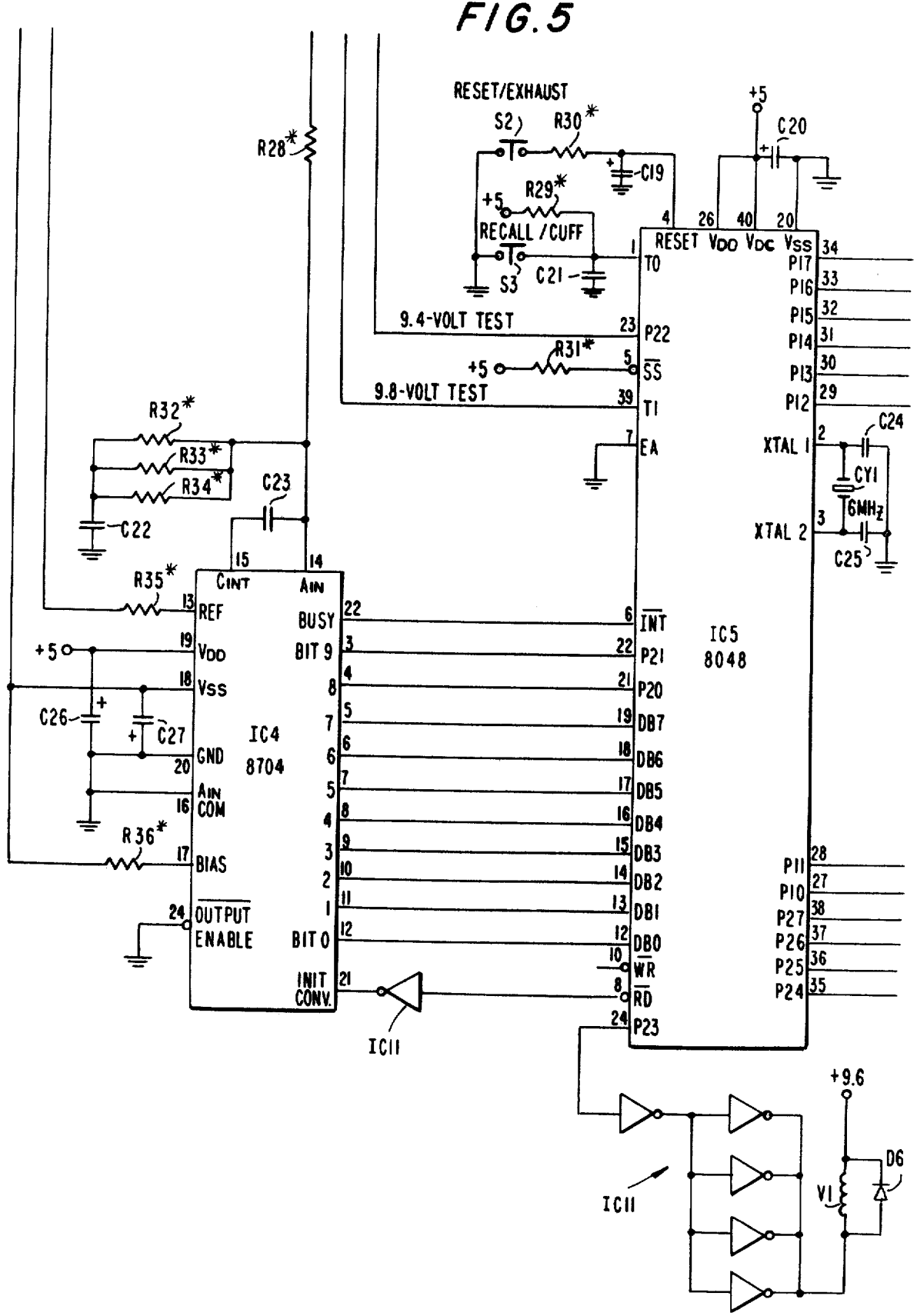

On FIG. 5, chip IC4 is a Teledyne 8704 analog-to-digital converter, arranged in a standard configuration. The chip is interfaced directly to chip IC5, an Intel 8048 microprocessor with on-board ROM and RAM. The analog signal which is to be converted to a digital sample appears at pin 14 of chip IC4. The converter generates a 10-bit sample at pins 3-12. The data bus of the microprocessor has only 8 lines, DB0-DB7, and consequently only the eight least significant bits of each sample are connected to the data bus inputs of the microprocessor. The two most significant bits, 8 and 9, are extended to the bit 0 and bit 1 inputs of port 2 of the microprocessor, pins 21 and 22. The microprocessor reads in one sample at the same time that it initiates the formation of a new one, i.e., at the same time that it initiates a new conversion cycle. During normal processing, the microprocessor is so fast that it is ready for another sample even before the converter has one available. During the course of a conversion, the BUSY output of the converter is high. This output is connected to the $\overline{INT}$ input of the microprocessor, and the microprocessor polls this input, remaining in a wait loop, until the BUSY signal eventually goes low at the end of conversion cycle. At this time, a new sample appears at the outputs of the converter, and the microprocessor initiates the reading in of the new sample by reading in the bit values at port 2 (the two most significant bits of the new sample appear at the bit 0 and 1 positions of the port). The microprocessor then reads in the eight remaining bits in the new sample (which remain available at the output pins of the converter until the next conversion is over), by reading in the eight bits which appear at the DB0-DB7 data bus pins. The read instruction which is executed results in the $\overline{RD}$ output (pin 8) of the microprocessor going low. One of the inverters in chip IC11 inverts this low signal and applies a high potential to the "initiate conversion" input of the converter. This causes the converter to take a new sample, and its BUSY output goes high. Thereafter, the microprocessor proceeds with its processing of the new sample until it is ready to read in a new sample. The 8048 chip polls the $\overline{INT}$ input, which is high as long as a conversion cycle is in progress, and the microprocessor remains in a wait loop. Only when a new sample is available at the 10 output pins of the converter does the BUSY signal go low and the microprocessor actually read in a new sample.

The sampling rate is thus dependent upon how fast the converter can generate samples. In the illustrative embodiment of the invention, samples are generated approximately every 2.5 milliseconds. This is a sufficiently high sampling rate; if a typical blood pressure pulse has a duration of 100 milliseconds, about 40 samples will be taken during its course—more than enough to completely define the pulse waveshape.

Only a brief description of the 8048 microprocessor will be given in view of its widespread use in industry. A complete description of the unit may be found in the 1979 Intel Corporation Publication entitled "MCS-48 Family of Single Chip Microcomputers User's Manual".

It should be noted that the unit is actually referred to by its manufacturer as a microcomputer, not a microprocessor. This is due to the fact that it includes on-board memory—1k of program memory (ROM) and 64 data memory locations (RAM). All memory locations have 8 bits.

The 64 locations of the data memory are indirectly addressable through either of two RAM pointer registers at addresses 0 and 1—registers R0 and R1. The first eight locations 0-7 of the data memory are designated as working registers, and are directly addressable by several of the instructions which the chip can execute. When the Register Bank Switch instruction is executed, data memory locations 34-41 become the working registers instead of locations 0-7. It is only these registers which are then directly addressable. When the second register bank is selected as the working registers, the registers at addresses 24 and 25, R0' and R1', can be used as pointer registers.

RAM locations 8-23 serve in a dual capacity—they cannot only be used for any purpose desired, but they also serve as the program counter stack; they are addressed by the stack pointer during subroutine calls and returns as well as by pointer registers R0, R1, R0' and R1'. When the system is reset by applying a low potential to pin 4 of the chip, the program counter is reset to zero so that the first instruction which is fetched is that from location 0 is the program memory. In addition, the stack pointer (a 3- bit register in the Program Status Word) is initialized to zero, and points to RAM locations 8 and 9. Each subroutine call or interrupt results in the program counter contents (12 bits) and 4 bits of the Program Status Word being transferred to the two locations pointed to by the stack pointer, and the stack pointer is then incremented so that it points to the next two locations (10 and 11, following 8 and 9). A return from subroutine or interrupt processing results in decrementing of the stack pointer and then restoration to the program counter and the Program Status Word of the two previously stored bytes.

The 8048 has two 8-bit ports, P1 and P2. In FIG. 5, a pin label such as P26 identifies the sixth bit of port 2. Data written to a port is latched and remains unchanged until re-written. But even though the ports latch on output, they can also be used as non-latching inputs. In this sense, the ports are quasi-directional. This feature is used to advantage because the microprocessor need not utilize the data memory to store information which is actually latched at the two output ports; if the microprocessor requires this information, it can simply read it in. Thus the ports serve not only as inputs and outputs, but in a sense they also serve as memory.

The BUS is an eight-bit port (DB0-DB7) which is a true bi-directional port which can be strobed for input and output. Data are written and latched by using the OUTL instruction, and are inputted by using the INS instruction. It is when the INS instruction is executed that the $\overline{RD}$ output is pulsed low. It will be recalled from the description above of the interface between the analog-to-digital converter and the microprocessor that the reading in of the eight least significant bits of a sample (the second step of the overall reading in of a sample) is accompanied by the pulsing of the $\overline{RD}$ output of the microprocessor and the initiation of a new conversion cycle.

There are three pins which serve as inputs and are testable with conditional jump instructions. The three pins are T0, T1 and $\overline{INT}$. The $\overline{INT}$ input can also control interrupts when it goes low, provided that interrupts are enabled under program control; they are not thus enabled in the blood pressure measuring instrument, and the INT is simply used as are the T0 and T1 inputs.

The processor includes two flags F0 and F1. These flags may be set under program control, and then tested to control branches.

The chip also includes a timer/counter, which functions as a timer in the illustrative embodiment of the invention. Separate instructions enable the timer/counter and start automatic incrementing of a count under timer control. The counter is initialized such that the counter overflows every 800 microseconds. Overflow of the counter controls an automatic jump to location 7 in the program memory. In the system of FIGS. 3–6, the timer/counter is used to time 800-microsecond intervals; a single character position of the display is updated or refreshed every 800 microseconds, the entire display being changed or refreshed every 9.6 milliseconds.

The 8048 chip is provided with a self-contained clock, which requires a crystal between pins 2 and 3. A 6-MHz crystal is used in the system of FIGS. 3–6, this being the recommended crystal frequency.

Referring to FIG. 5, switch S2 is the reset switch and is coupled through resistor R30 to the reset input, pin 4, of chip IC5. When the reset button is depressed, the microprocessor is reset and the program counter is loaded with a value of zero. The recall/cuff switch S3 similarly applies a ground potential to test input T0, pin 1, when it is depressed to control one of two different operations depending upon the state of the system when the switch is operated, as described above.

The 9.8-volt test line is connected to the T1 test input. When this input is tested, a high level (1) indicates that the battery potential exceeds 9.8 volts, and a low level (0) indicates that it does not. The 9.4-volt test line is connected to pin 23, bit 2 of port 2. When port 2 is read and bit 2 is examined, the system can determine whether the battery potential is greater or less than 9.4 volts.

As described above, the BUSY output of chip IC4 is used as the $\overline{INT}$ test input of chip IC5. The microprocessor remains in a wait loop until the BUSY output of the converter goes low, indicating that a new sample is available. When the microprocessor first reads in port 2, the two bit values at bits 0 and 1 represent the two most significant bits of the latest sample. Thereafter, the eight BUS inputs are read in to determine the eight least significant bits, and the pulsing low of the $\overline{RD}$ output of the microprocessor initiates a new conversion cycle.

Pin 24 is the bit 3 pin of port 2. As long as this pin is high in potential, five of the inverters of chip IC11 apply a high potential to the lower end of the energizing coil of normally-open valve V1. As a result, no current flows through the coil and the valve remains open. But a low potential at bit 3 of port 2 causes a low potential to be applied to one end of the energizing coil, current flows through it, and the valve closes. When the system is initialized upon reset, all of the port outputs are forced high, and thus initially the valve is open to vent the cuff to the atmosphere. It should be noted that four inverters are connected in parallel at the bottom of FIG. 5 in order to provide a sufficient sink for the current which closes the valve.

Bits 4-7 of port 2 (pins 35-38) are used to identify one of the twelve positions of the display. The microprocessor selects a position for up-dating or refreshing by applying an appropriate 4-bit code to pins 35–38. (Of the 16 possible codes, the microprocessor applies only 12 in sequence since the display has only 12 character positions.) The bit outputs are inverted by respective inverters in chip IC7, and the inverted bit values are applied to pins 12–15 of chip IC9 on FIG. 6. This latter chip energizes one of its 12 outputs depending upon the four-bit code outputted at bits 4–7 of port 2. Display element DP1 has 12 seven-segment displays (see FIG. 9) and, in order to energize selected segments at any particular position, it is necessary to energize the cathode at that position. Decoder chip IC9 controls the energization of only one cathode at any given time.

The particular anode segments which are selected to be illuminated are represented by the seven least significant bits of port 1, at pins 27-33. Each of these bits is inverted by an inverter in either chip IC6 or chip IC7, and the seven inverted segment bits are applied to inputs of respective amplifiers in chip IC8. The most significant bit at port 1 determines whether the pulse light LD1 is to be illuminated. The bit at pin 34 of the microprocessor is similarly inverted in chip IC6 and is amplified by one of the inverters in chip IC8. Of the eight outputs of chip IC8, seven are extended to display DP1 for controlling selected energizations of the seven segments at the position determined by decoder IC9. The eighth output of chip IC8 is extended to the anode of the pulse light LD1 for controlling its illumination during either the presence of a pulse, or after final measurement results have been displayed for ten seconds and the display has been blanked.

Figure 8:
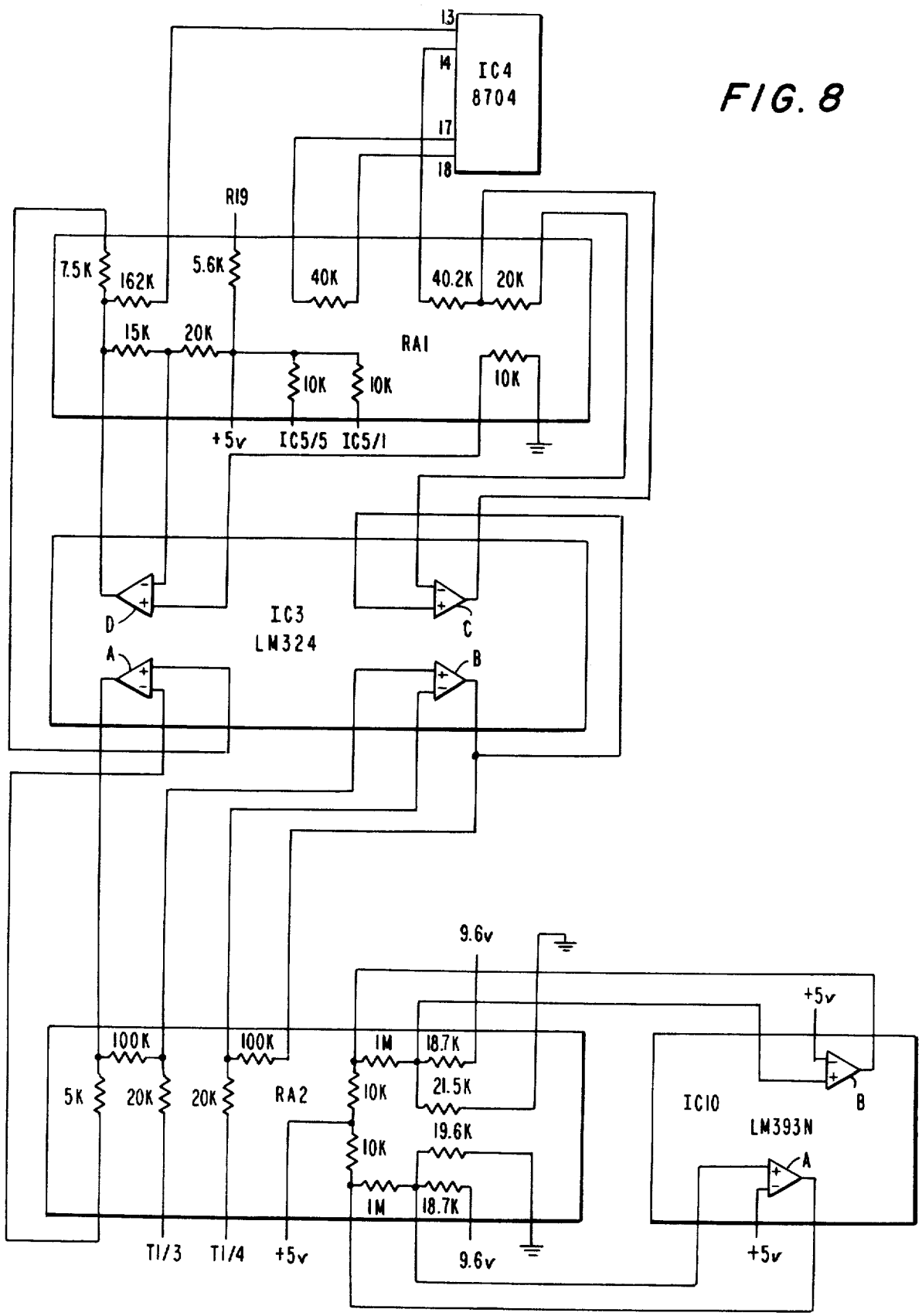
FIG. 8 depicts two resistor networks utilized in the circuit of FIGS. 3-6.

All of the resistors which are marked with asterisks in FIGS. 3–6 are included on resistor networks and have a precision of 1%. The list of component values above identifies the resistors included in each of networks RA1-RA4. As indicated at the end of the component list, network RA3 is a standard ten-pin, single-in-line package; it has five resistors each of magnitude 330 ohms. Network RA3 is a similar package having five 4.7 k resistors. Networks RA1 and RA2 are both custom 16-pin, dual-in-line packages. FIG. 8 depicts the network configuration for both RA1 and RA3, and the manner in which the internal resistors are connected to certain of the other chips. It should be noted that although network RA1 is provided with 16 pins, only fifteen of them are used. A spare resistor may be fabricated on the chip if required, e.g., another 10 k resistor may be connected in parallel with the two which are connected to pins 1 and 5 of chip IC5.

Throughout the remaining description, reference is made to the firmware source statements. The listing was generated using the Intel INTELLEC microcomputer development system, utilizing the macro assembler identified at the top of the listing. The source statements themselves are in the center, and each statement is numbered consecutively. In the rightmost column there are comments which will be helpful in understanding the firmware, although all statements are described below. The two leftmost columns provide the assembled object code and the ROM location of each byte. The listing thus presents the complete ROM code for the microprocessor chip. For an understanding of the present invention, however, it is necessary to analyze the source statements—and then only the source statements which pertain to the invention; in the Croslin application, the entire listing is described since that application is directed to the blood pressure measuring methodology. The assembly listing consists of 19 pages, as follows:

```
ASM48  :F1:BP9.SRC TITLE ('ESM-410 BP9.LST REV 0 06/12/79 PROM 43')

ISIS-II MCS-48/UPI-41 MACRO ASSEMBLER, V2.0           PAGE    1
ESM-410 BP9.LST REV 0 06/12/79 PROM 43

LOC  OBJ         SEQ        SOURCE STATEMENT

1  $       DEBUG MACROFILE PAGEWIDTH (80)
                  2
                  3  ;       BLOOD PRESSURE MACHINE PROGRAM
                  4  ;       ESM 400 SERIES
                  5  ;       COPYRIGHT 1979- MEDTEK CORPORATION
                  6
                  7  ;       PULSE AMPLITUDE TESTING ASSIGNMENTS
                  8
 00FF             9  TRUE    EQU     0FFH
 0000            10  FALSE   EQU     0H
 0000            11  TEST    EQU     FALSE
                 12
                 13  ;       BANK 0 ASSIGNMENTS
                 14
                 15  ;       P0 AND P1 USED AS GENERAL POINTERS
                 16
 0002            17  AP2     EQU     R2
 0003            18  HMAX    EQU     R3        ; MAXIMUM HEIGHT
 0004            19  PLSCNT  EQU     R4        ; PULSE COUNT
 0005            20  COUNT   EQU     R5        ; COUNTER
 0006            21  PLSVLD  EQU     R6        ; VALID PULSE COUNT
 0007            22  TENSEC  EQU     R7        ; TEN SECONDS UP
                 23
                 24  ;       BANK 1 ASSIGNMENTS
                 25
                 26  ;       R2,R3 USED FOR REFERENCE PRESSURE
                 27
 0000            28  SEGPTR  EQU     R0        ; CHAR SEGMENT POINTER
 0001            29  DIGSAV  EQU     R1        ; DIGIT # SAVE
 0004            30  HUN3    EQU     R4        ; PLS MSEC COUNTER
 0005            31  HUN1    EQU     R5        ; MSEC COUNTER
 0006            32  HUN2    EQU     R6        ; SEC COUNTER
 0007            33  ASAV    EQU     R7        ; SAVE ACC HERE
                 34
```

```
                            35 ; MEMORY STORAGE
                            36
0018                        37              ORG     18H
                            38
0001            39 SGPTR:    DS      1                  ; ALT REF TO SEGPTR
0001            40           DS      1                  ; DIGIT # SAVE
0002            41 PREF:     DS      2                  ; REFERENCE PRESSURE
0001            42 AUX33:    DS      1                  ; ALT REF TO AUX3
0001            43 AUX11:    DS      1                  ; ALTERNATE REF TO AUX1
0001            44 AUX22:    DS      1                  ; ALTERNATE REF TO AUX2
                            45
0020                        46              ORG     20H
                            47
0002            48 SYS:      DS      2                  ; SYSTOLIC PRESSURE
0002            49 DIA:      DS      2                  ; DIASTOLIC PRESSURE
0002            50 PTMP:     DS      2                  ; TEMP PRESS STORAGE
0002            51 BCD:      DS      2                  ; BCD NUMBER
0004            52 HTBL:     DS      4                  ; PULSE HEIGHT
```

ISIS-II MCS-48/UPI-41 MACRO ASSEMBLER, V2.0                              PAGE   2
ISM-410 RP9 LST REV 0 06/12/79 PROM 42

LOC  OBJ             SEQ          SOURCE STATEMENT

```
002B            53 H0        EQU     HTBL+3            ; LAST PULSE HEIGHT
0008            54 PTBL:     DS      8                 ; PRESSURES
0012            55 PLAST     EQU     PTBL+6            ; LAST PRESS BEFORE PLS
0010            56 DTBL:     DS      12                ; SEGMENT TABLE
                            57
0028            58 H1        EQU     HTBL
0029            59 H2        EQU     HTBL+1
002A            60 H3        EQU     HTBL+2
002B            61 H4        EQU     HTBL+3
                            62
002C            63 PR1       EQU     PTBL
002E            64 PR2       EQU     PTBL+2
0030            65 PR3       EQU     PTBL+4
0032            66 PR4       EQU     PTBL+6
002C            67 PMAX      EQU     PTBL
002E            68 PMIN      EQU     PTBL+2
                            69
                            70 ; SET BEGINNING OF PAGE 3 FOR MESSAGES
                            71
0300            72 PG3       EQU     300H
                            73
                            74 ; START OF PROGRAM
                            75
0000                        76              ORG     0
                            77
0000 23F6       78 START:    MOV     A,#10            ; INITIALIZE TIMER
0002 62         79           MOV     T,A
0003 B919       80           MOV     R1,#SGPTR        ; INIT DISPLAY SEG PTR
0005 041E       81           JMP     SEGSET
                            82
                            83 ; TIMER INTERRUPT SUBROUTINE
                            84
0007                        85              ORG     7
                            86
0007 D5         87 TIMER:    SEL     RB1              ; REGISTER BANK 1
0008 AF         88           MOV     HSAV,A           ; SAVE ACCUMULATOR
0009 23F6       89           MOV     A,#10            ; 800 USEC TIMER
000B 62         90           MOV     T,A
000C 5442       91           CALL    SEGS             ; NEXT CHARACTER
000E FC         92           MOV     A,AUX3           ; PLS WIDTH TIMER
000F 0612       93           T2      MCHK
0011 CC         94           DEC     AUX3
0012 EC1B       95 MCHK:     DJNZ    AUX1,TIMINT      ; DEC MSEC COUNTER
0014 BD7D       96           MOV     AUX1,#125        ; 100 MSEC
0016 FE         97           MOV     A,AUX2           ; SEC COUNTER
0017 C61A       98           JZ      TIMINT           ; TIME ELAPSED?
0019 CE         99           DEC     AUX2
001A 1610      100 TIMINT:   JTF     TESTT            ; RESET TIMER OVERFLOW
001C FF        101 TESTT:    MOV     A,HSAV           ; RESTORE ACCUMULATOR
001D 93        102           RETR
```

```
104  ;  ENDROS
105
106  ;  COMPARE TWO SINGLE BYTE QUANTITIES
107
```

ISIS-II MCS-48/UPI-41 MACRO ASSEMBLER, V2.0                    PAGE    3
M-410 BP9.LST REV 0 06/12/79 PROM 43

```
LOC  OBJ         SEQ         SOURCE STATEMENT

108 CMPH    MACRO   HX, HY
                 109         MOV     A, #HX
                 110         MOV     R1, #HY
                 111         CALL    MINV
                 112         ENDM
                 113
                 114  ;  INITIALIZE DISPLAY AND TIMER
                 115
001E B034        116 SEGSET: MOV     @R0, #DTEL
0020 2378        117         MOV     A, #CAL-PG3      ; "CAL"
0022 3408        118         CALL    DALPHA
0024 25          119         EN      TCNTI
0025 55          120         STRT    T                ; START TIMER
                 121
                 122  ;  DELAY 1 SEC, GET REFERENCE PRESSURE
                 123
0026 54F0        124         CALL    WT1SEC
0028 08          125         INS     A, BUS           ; INITIAL INIT CONV
0029 74F5        126 AMBCHK: CALL    REFP             ; REF PRESS
                 127
                 128  ;  CALIBRATE MODE AND BATTERY CHECK
                 129
002B 0A          130 P40     IN      A, P2            ; CHECK CAL SWITCH
002C 124A        131         JB2     DELCHK           ; BATT OK, NOT CAL
002E 464A        132         JNT1    DELCHK           ; BRANCH IF BATT LOW
0030 9AF7        133         ANL     P2, #0F7H        ; CLOSE VALVE
                 134
                 135  ;  FACTORY CALIBRATE MODE
                 136
0032 0406        137 CHLIB:  CALL    DPRESS           ; "PRESS"
0034 B93C        138 CHLMIN: MOV     R1, #DTEL+8      ; PUT "-" HERE
0036 B0BF        139         MOV     @R1, #0BFH       ; "-" SEGMENTS
0038 54FA        140 CHLCON: CALL    READP            ; READ PRESSURE
003A 27          141         CLR     A
003B F644        142         JC      CALPOS           ; PRESSURE NEG?
003D 25          143         CPL     A
003E 547E        144         CALL    DMOVE            ; - 2X PRESS
0040 5476        145         CALL    DMINC            ; -PRESS + 2X PRESS
0042 54E9        146         CALL    DST              ; PTMP
0044 5410        147 CALPOS: CALL    DSPRES           ; DISPLAY PRESSURE
0046 B624        148         JF0     CHLMIN
0048 0438        149         JMP     CHLCON
                 150
                 151  ;  CHECK IF DELTA PRESSURE > 1.0 MM HG
                 152
004A 54CA        153 DELCHK: CALL    BDEAD            ; BATTERY DEAD?
004C 54F0        154         CALL    WT1SEC
004E 54FA        155         CALL    READP
0050 B932        156         MOV     R1, #PLAST       ; SAVE LAST PRESS RDG
0052 24EC        157         CALL    DMOVE
0054 54FA        158         CALL    READP
0056 B932        159         MOV     R1, #PLAST
0058 5470        160         CALL    DMINV            ; PTMP - PLAST
005A E25F        161         JB     DELTA             ; BRANCH IF DELTA >=0
005C 37          162         CPL    A                 ; 2'S COMP IF NEG
```

ISIS-II MCS-48/UPI-41 MACRO ASSEMBLER, V2.0                    PAGE    4
ESM-410 BP9.LST REV 0 06/12/79 PROM 43

```
LOC  OBJ         SEQ         SOURCE STATEMENT 005D 17          163         INC     A
005E D3FF        164 DELTA:  ADD     A, #0142         ; DELTA P : 1.0 MM HG
0060 F629        165         JC      AMBCHK           ; BRANCH IF >= 1 MM HG
```

```
166
167 ; CHECK IF BATTERY LOW OR OK  IF BATTERY LOW,
168 ; MESSAGE IS "LO DC", ELSE "CUFF"
169
0062 232F         170         MOV     A, #CUFF-PG3    ; "CUFF"
0064 5668         171         JT1     MCUFF           ; BRANCH IF BATT OK
0066 2D7H         172         MOV     A, #LOBATT-PG3  ; "LO DC"
0068 5408         173 MCUFF:  CALL    DALPHA
             174
             175 ; CHECK IF PUMPING BEFORE RECALL/CUFF DEPRESSED
             176
006A 540A         177 LOOP:   CALL    BCHK            ; CHECK BATTERY
006C 24FA         178         CALL    READP           ; GET PRESSURE
006E E67E         179         JNC     CLOSE           ; PRESS NEG?
0070 230A         180         MOV     A, #10+2        ; PRESS > 10 MM HG
0072 B900         181         MOV     AE0, #0H
0074 5476         182         CALL    DMINC
0076 E67E         183         JNC     CLOSE           ; BRANCH IF < 10 MM HG
0078 232F         184 LOOP1:  MOV     A, #CUFF-PG3
007A 5408         185         CALL    BLINK
007C 0478         186         JMP     LOOP1
007E 266A         187 CLOSE:  JT0     LOOP            ; RECALL/CUFF?
0080 74E5         188         CALL    REFP            ; NEW REF PRESS
0082 98F7         189         ANL     P2, #0F7H       ; CLOSE VALVE
0084 2340         190 PUMP1:  MOV     A, #OCCL-PG3    ; "OCCLUDE"
0086 5408         191         CALL    DALPHA
             192
             193 ; OCCLUDING PRESSURE > 40 CHECK
             194
0088 24FA         195 PUMP2:  CALL    READP           ; READ PRESSURE
008A E688         196         JNC     PUMP2           ; PRESSURE NEG?
008C 2350         197         MOV     A, #40+2        ; COMPARE WITH 40 MM HG
008E B900         198         MOV     AE0, #0
0090 5476         199         CALL    DMINC
0092 E688         200         JNC     PUMP2           ; PTMP < 40
0094 BDFF         201         MOV     COUNT, #0FFH    ; "PRESS" FLAG
             202
             203 ; OCCLUDE PRESSURE CHECK
             204
0096 B92C         205 PSTTMP: MOV     R1, #PMAX       ; INITIAL PMAX
0098 74EC         206         CALL    DMOVE
009A B92E         207         MOV     R1, #PMIN       ; INITIAL PMIN
009C 74EC         208         CALL    DMOVE
009E B91E         209 PUMP3:  MOV     R1, #OCC22      ; 2.5 SECS
00A0 B119         210         MOV     @R1, #25
00A2 85           211 PUMP4:  CLR     F0              ; CLEAR PULSE FLG
00A3 23F4         212 PUMP1:  MOV     A, #244         ; PRESS > 250?
00A5 B901         213         MOV     AE0, #1
00A7 5476         214         CALL    DMINC
00A9 E6B3         215         JNC     OCCOK1          ; HI OCC PRESS IF >250
00AB 2746         216         MOV     A, #OCCPR-PG3
00AD 5408         217         CALL    DALPHA
```

ISIS-II MCS-48/UPI-41 MACRO ASSEMBLER, V2.0           PAGE    5
ESM-410 BP9.LST REV 0 06/12/79 PROM 43

```
LOC  OBJ          SEQ             SOURCE STATEMENT

00AF BDFF         218         MOV     COUNT, #0FFH    ; SET "PRESS" FLAG
00B1 04BC         219         JMP     OCCOK
00B3 FD           220 OCCOK1: MOV     A, COUNT        ; CHECK "PRESS" FLAG
00B4 C6BA         221         JZ      OCCOK2
00B6 BD00         222         MOV     COUNT, #0       ; CLR "PRESS" FLAG
00B8 5406         223         CALL    DPRESS          ; "PRESS"
00BA 5410         224 OCCOK2: CALL    DSPRES
00BC 24FA         225 OCCOK:  CALL    READP           ; NEXT READING
00BE 2346         226         MOV     A, #35+2        ; PRESS <35 CHECK
00C0 B900         227         MOV     AE0, #0
00C2 5476         228         CALL    DMINC
00C4 E684         229         JNC     PUMP1
             230
             231 ; NEW MAXIMUM PRESSURE CHECK
             232
00C6 B92C         233         MOV     R1, #PMAX       ; MAX PRESSURE
00C8 5470         234         CALL    DMINV           ; PTMP-PMAX
```

```
00CH F696      235           TO       PSTTMP      ; RESET TIMER, PLS,AMPL
00CC B92E      236 PLTPMX:   MOV      P1, #PMIN   ; PTMP-PMIN
00CE 5470      237           CALL     DMINV
00D0 E6DF      238           JNC      NEWMIN      ; CHECK MAX HEIGHT
00D2 B6D2      239           JF0      PNEXT       ; PULSE ALREADY FOUND
00D4 03FE      240           ADD      A, -#2      ; HOW BIG
00D6 F2D3      241           JB7      PNEXT       ; < 1 MM HG
00D8 95        242           CPL      F0          ; SET PULSE FLAG
00D9 B91C      243           MOV      P1, #AUX33  ; PW TIMER
00DB B14B      244           MOV      @P1, #75    ; 60 MSEC
00DD 04B2      245           JMP      PNEXT
00DF 74EC      246 NEWMIN:   CALL     DMOVE       ; PMIN=PTMP
00E1 B91C      247           MOV      P1, #AUX33  ; PW CHECK
00E3 B6E7      248           JF0      PUMP5
00E5 04EA      249           JMP      PUMP6
00E7 F1        250 PUMP5:    MOV      A, @P1
00E8 C6F1      251           JZ       PUMP7
00EA B91E      252 PUMP6:    MOV      P1, #AUX22
00EC F1        253           MOV      A, @P1
00ED 96A2      254           JNZ      PUMP4
00EF 2401      255           JMP      INITPS
               256
               257 ; OCCLUDE PRESSURE TOO LOW
               258
00F1 BDFF      259 PUMP7:    MOV      COUNT, #0FFH ; SET "PRESS" FLAG
00F3 2340      260           MOV      A, #LOCCPR-PG3
00F5 5408      261           CALL     DALPHA
               262
               263 ; WAIT UNTIL PTMP >= PMAX
               264
00F7 34FA      265 NEWOCC:   CALL     PEADP
00F9 B92D      266           MOV      P1, #PMAX   ; COMPARE PTMP:PMAX
00FB 5470      267           CALL     DMINV
00FD E6F7      268           JNC      NEWOCC      ; PTMP>PMAX?
00FF 049E      269           JMP      PUMP3
               270
               271 ; SET PULSE COUNT TO MINUS 2 TO IGNORE FIRST TWO PULSES
               272 ; FOR COUNTING PULSES ONLY

[ISIS-II] MCS-48/UPI-41 MACRO ASSEMBLER, V2.0                    PAGE   6
ESM-410 BP9.LST REV 0 06/12/79 FROM 42

LOC  OBJ       SEQ           SOURCE STATEMENT 273
0101 B1FF      274 INITPS:   MOV      @P1, #255   ; SEC TIMER <> 0
0103 5406      275           CALL     DPRESS      ; "PRESS"
0105 5410      276           CALL     DSPPES
0107 BCFE      277 SYST0:    MOV      PLSCNT, -#2
               278
               279 ; SYSTOLIC PRESSURE
               280 ; DETECT FIRST FOUR PULSES, DISCARD IF DELTA PRESS >= 1
               281
0109 27        282           CLR      A
010A AE        283           MOV      PLSVLD, A   ; SET PLSVLD FALSE
010B AF        284           MOV      TENSEC, A   ; SET TENSEC FALSE
010C BC04      285 SYST:     MOV      COUNT, #4   ; FOUR PULSES
010E 7453      286 SYST1:    CALL     PLS
0110 FD        287           MOV      A, COUNT    ; 2 PULSES YET?
0111 03FC      288           ADD      A, -#4
0113 C61F      289           JZ       SYST2
0115 B830      290           MOV      P0, #PP3    ; PR3-PR4
0117 B932      291           MOV      P1, #PP4
0119 5470      292           CALL     DMINV
011B 03EC      293           ADD      A, -#10+2   ; DELTA >= 10?
011D F607      294           TC       SYST0
011F ED0E      295 SYST2:    DJNZ     COUNT, SYST1 ; COLLECTED 4 PULSES?
               296
               297 ; CHECK PULSE AMPLITUDES FOR VALID SYSTOLIC CRITERIA
               298
               299           CMPH     H2, H1
0121 B829      300+          MOV      P0, #H2
0123 B928      301+          MOV      P1, #H1
0125 34E9      302+          CALL     MINV
0127 E643      303           JNC      H1GTH2      ; BRANCH IF H1>H2
```

```
                       304            CMPH      H2, H2
0129 B82A              305+           MOV       P0, #H3
012B B929              306+           MOV       P1, #H2
012D 24E9              307+           CALL      MINV
012F F652              308            JC        HMAXI        ; BRANCH IF H2<=H3
                       309 H13CHK:    CMPH      H2, H1
0131 B82A              310+           MOV       P0, #H3
0133 B928              311+           MOV       P1, #H1
0135 24E9              312+           CALL      MINV
0137 E6D1              313            JNC       SYSER        ; ERROR IF H1>H3
                       314            CMPH      H4, H2
0139 B82B              315+           MOV       P0, #H4
013B B929              316+           MOV       P1, #H2
013D 24E9              317+           CALL      MINV
013F E6D1              318            JNC       SYSER        ; ERROR IF H2>H4
0141 2453              319            JMP       HMAXI
                       320 H10TH2:    CMPH      H3, H2
0143 B82A              321+           MOV       P0, #H3
0145 B929              322+           MOV       P1, #H2
0147 24E9              323+           CALL      MINV
0149 E6D1              324            JNC       SYSER        ; ERROR IF H2>H3
                       325            CMPH      H4, H3
014B B82B              326+           MOV       P0, #H4
014D B92A              327+           MOV       P1, #H3
```

ISIS-II MCS-48/UPI-41 MICRO ASSEMBLER, V2.0                          PAGE    7
BSM-410 BP9.LST REV 0 06/12/79 PROM.43

LOC    OBJ           SEQ            SOURCE STATEMENT

```
014F 24E9              328+           CALL      MINV
0151 E6D1              329            JNC       SYSER        ; ERROR IF H3>H4
0152 3406              330 HMAXI:     CALL      HSUM         ; INITIAL HMAX
0155 A8                331            MOV       HMAX, A
                       332
                       333 ; SYSTOLIC AMPLITUDE LIMIT CHECK
                       334
0156 03E8              335            ADD       A, -#24
0158 F6D1              336            JC        SYSER
015A B83A              337            MOV       P0, #PR3
015C B920              338            MOV       P1, #SYS     ; SYS = PR3
015E 74EC              339            CALL      DMOVE
                       340
                       341 ; DIASTOLIC
                       342
                       343 ; COUNT NUMBER OF PULSES AFTER MEAN
                       344 ; ARTERIAL PRESSURE
                       345
0160 BDFC              346 DIASCT:    MOV       COUNT, -#4   ; 4 PULSES AFTER MAP
0162 7453              347 DIAS:      CALL      PLS          ; NEXT PULSE
0164 3406              348            CALL      HSUM         ; NEW AMPL SUM
0166 F8                349            MOV       A, HMAX      ; IS IT MAXIMUM?
0167 37                350            CPL       A
0168 17                351            INC       A
0169 6A                352            ADD       A, HEX       ; HSUM-HMAX
016A F270              353            JB7       PLSCHK       ; BRANCH IF NOT MAX
016C FA                354            MOV       A, HEX       ; GET MAX AMPLITUDE
016D A8                355            MOV       HMAX, A      ; NEW MAXIMUM
016E 2460              356            JMP       DIASCT       ; NEXT PULSE
                       357
                       358 ; DO NOT CHECK FOR DIASTOLIC UNTIL 4 PULSES AFTER MEAN
                       359 ; ARTERIAL PRESSURE HAVE BEEN DETECTED
                       360
0170 1D                361 PLSCHK:    INC       COUNT
0171 FD                362            MOV       A, COUNT     ; BRANCH IF < 4
0172 F262              363            JB7       DIAS
                       364
                       365 ; AFTER A MAXIMUM IS FOUND, DIASTOLIC IS FOUND WHEN 4
                       366 ; CONSECUTIVE PULSE AMPLITUDE SUM < THRESHOLD.
                       367
0174 3406              368            CALL      HSUM         ; ADD AMPLITUDES
                       369
                       370 ; HMAX >= 9 FOR VALID CALCULATIONS
                       371
0176 F8                372            MOV       A, HMAX
```

```
0177 0307        373            ADD     A, -#9
0179 E662        374            JNZ     DIAS
                 375
                 376  ; DIASTOLIC THRESHOLD AS A FUNCTION OF HMAX:
                 377  ;         THRESHOLD = HMAX/2] + 4
                 378
017B FE          379  HMXSUB:   MOV     A, HMAX
017C 97          380            CLR     C
017D 67          381            RRC     A                   ; HMAX/2]
017E 0303        382            ADD     A, #3               ; HMAX/2] + 3
```

ISIS-II MCS-48/UPI-41 MACRO ASSEMBLER, V2.0                    PAGE    8
ESM-410 BP9.LST REV 0 06/12/79 PROM 43

LOC  OBJ         SEQ            SOURCE STATEMENT

```
0180 37          383            CPL     A                   ; -(HMAX/2] + 4)
0181 60          384  TSHCHK:   ADD     A, HEX              ; SIGMA - THRESHOLD
0182 F662        385            JB7     DIAS                ; BRANCH IF SIG > THR
0184 B82E        386            MOV     R0, #PR2            ; DIASTOLE = PR2
0186 B922        387            MOV     R1, #DIA
0188 74EC        388            CALL    DMOVE
018A FE          389  TIMEUP:   MOV     A, PLSVLD           ; VALID PULSE COUNT?
018B 9691        390            JNZ     PCNCHK
018D 7452        391            CALL    PLS
018F 248A        392            JMP     TIMEUP
                 393
                 394  ; PULSE COUNT: PMIN = 42, PMAX = 240
                 395
0191 23F9        396  PCNCHK:   MOV     A, -#7              ; .MIN PLS = 42
0193 6C          397            ADD     A, PLSCNT           ; 10 SEC PLS COUNT
0194 F29A        398            JB7     PLSNG               ; PULSE COUNT LOW
0196 03DE        399            ADD     A, -#34             ; MAX PLS = 240
0198 F2A4        400            JB7     PLSCLC              ; BRANCH IF < 41
                 401
                 402  ; PULSE ERROR MESSAGE: " ---"
                 403
019A 23EE        404  PLSNG:    MOV     A, #0EEH            ; " -"
019C BAEE        405            MOV     HEX, #0EEH          ; "---"
019E B826        406            MOV     R0, #BCD0
01A0 54E9        407            CALL    DST
01A2 24B0        408            JMP     PLSDSP
                 409
                 410  ; 6X PLSCNT
                 411
01A4 FC          412  PLSCLC:   MOV     A, PLSCNT           ; ACC = PLSCNT
01A5 6C          413            ADD     A, PLSCNT           ; 2X PLSCNT
01A6 6C          414            ADD     A, PLSCNT           ; 3X PLSCNT
01A7 F7          415            RLC     A                   ; 6X PLSCNT
01A8 BA00        416            MOV     HEX, #0
01AA B824        417            MOV     R0, #PTMP           ; SAVE PULSE COUNT
01AC 54E9        418            CALL    DST
01AE 5486        419            CALL    BINBCD1
01B0 2320        420  PLSDSP:   MOV     A, #DTBL+8
01B2 5416        421            CALL    DBCD
01B4 B820        422            MOV     R0, #SYS            ; SYSTOLIC PRESSURE
01B6 5480        423            CALL    BINBCD
01B8 2324        424            MOV     A, #DTBL
01BA 5416        425            CALL    DBCD
01BC B822        426            MOV     R0, #DIA            ; DIASTOLIC PRESSURE
01BE 5480        427            CALL    BINBCD
01C0 2328        428            MOV     A, #DTBL+4
01C2 5416        429            CALL    DBCD
01C4 24D5        430            JMP     DSPEND
                 431
                 432  ; SUBROUTINES
                 433
                 434  ; ADD THE FOUR PULSE AMPLITUDES
                 435
01C6 27          436  HSUM:     CLR     A
01C7 B828        437            MOV     R0, #HTBL           ; PULSE AMPL TABLE
```

```
ISIS-II MCS-48/UPI-41 MACRO ASSEMBLER, V2.0                PAGE    9
ESM-410 BP9.LST REV 0 06/12/79 FROM 43

LOC  OBJ            SEQ          SOURCE STATEMENT

01C9 BA04           438          MOV     R2, #4
  01CB 60             439 HSUM1:   ADD     A, @R0          ; ADD THE AMPL'S
  01CC 18             440          INC     R0
  01CD EACB           441          DJNZ    R2, HSUM1
  01CF AA             442          MOV     R2, A           ; SAVE SUM
  01D0 83             443          RET
                      444
                      445 ; SYSTOLIC ERROR MESSAGE
                      446
  01D1 2320           447 SYSER:   MOV     A, #SYSERR-PG3  ; "SYS ERROR"
                      448
                      449 ; DISPLAY MESSAGE FOR 10 SECONDS AND WAIT FOR RECALL.
                      450 ; PULSE LITE ON CONTINUOUS AFTER 10 SECONDS.
                      451
  01D3 5408           452 DPECHL:  CALL    DALPHA
  01D5 8A08           453 DSPEND:  ORL     P2, #08H        ; OPEN VALVE
  01D7 89S0           454          ORL     P1, #80H        ; PLS LITE OFF
  01D9 2364           455          MOV     A, #100         ; TEN SECONDS
  01DB 54F2           456          CALL    WAIT
  01DD 25             457          DIS     TCNTI
  01DE 89FF           458          ORL     P1, #0FFH       ; DISPLAY LITE OFF
  01E0 9A0F           459          ANL     P2, #0FH        ; DIGIT # 15
  01E2 997F           460          ANL     P1, #7FH        ; LITE ON
  01E4 36E4           461 AGAIN:   JT0     AGAIN           ; RECALL?
  01E6 25             462          EN      TCNTI           ; ENABLE TIMER INT
  01E7 24D5           463          JMP     DSPEND
                      464
                      465 ; SINGLE PRECISION SUBTRACT
                      466
  01E9 F1             467 MINV:    MOV     A, @R1          ; 2'S COMPLEMENT
  01EA 37             468          CPL     A
  01EB 17             469          INC     A
  01EC 60             470          ADD     A, @R0
  01ED 83             471          RET
                      472
                      473 ; READ PRESSURE AND PLACE IN REX. A. VALUE IS TWICE
                      474 ; THE PRESSURE IN MM HG. "INS" SENDS INIT CONV COMMAND
                      475
  01EE 86F2           476 READPR:  JNI     GETP            ; CHECK IF BUSY IS LOW
  01F0 24EE           477          JMP     READPR          ; NO. TRY AGAIN
  01F2 0A             478 GETP:    IN      A, P2           ; A/D BITS 9,8
  01F3 5303           479          ANL     A, #03H
  01F5 AA             480          MOV     R2, A           ; STORE IN REX
  01F6 08             481          INS     A, BUS          ; A/D BITS 7-0
  01F7 B81A           482          MOV     R0, #PREF
  01F9 83             483          RET
                      484
                      485 ; PTMP = PRESSURE - REFERENCE PRESSURE IN 1/2 MM HG
                      486
  01FA 34EE           487 READP:   CALL    READPR
                      488
                      489 ; PRESSURE - PREF. STORE IN PTMP
                      490
  01FC B824           491 PPTMP:   MOV     R0, #PTMP       ; 2X PRESS IN PTMP
  01FE 54E9           492          CALL    DST

ISIS-II MCS-48/UPI-41 MACRO ASSEMBLER, V2.0                PAGE   10
ESM-410 BP9.LST REV 0 06/12/79 FROM 43

LOC  OBJ            SEQ          SOURCE STATEMENT

0200 B91A           493          MOV     P1, #PREF       ; 2X PREF
  0202 5470           494          CALL    DMINV           ; 2X (PTMP-PREF)
  0204 44E9           495          JMP     DST             ; STORE IN PTMP
                      496
                      497 ; DISPLAY "PRESS"
                      498
  0206 2349           499 DPRESS:  MOV     A, #PRESS-PG3   ; "PRESS"
                      500
                      501 ; SET UP ALPHA MESSAGE SEGMENTS
```

```
                              502 ;          AEX CONTAINS NUMBER BYTES - 1
                              503 ;          LOAD ACC WITH PAGE 3 MESSAGE ADDR, MOVED TO R1
                              504 ;          R1 CONTAINS DTBL ADDRESS
                              505
0208 B905                     506 DALPHA: MOV    AEX, #5         ; 6 BYTES
020A A8                       507         MOV    R0, A           ; MESG LOCATION
020B B924                     508         MOV    R1, #DTBL       ; FIRST DISPLAY LOCATION
020D A5                       509         CLR    F1              ; F1=0 FOR ALPHA
020E 4420                     510         JMP    DISP
                              511
                              512 ; DISPLAY PRESSURE
                              513
0210 B824                     514 DSPRES: MOV    R0, #PTMP
0212 5480                     515         CALL   BINBCD
0214 233C                     516 DSPRS1: MOV    A, #DTBL+8
                              517
                              518 ; SET UP BCD NUMBERS SEGMENTS:
                              519 ;          AEX CONTAINS NUMBER BYTES - 1
                              520 ;          R0 CONTAINS ADDRESS BCD0
                              521 ;          LOAD ACC WITH DTBL, DTBL+4, DTBL+8, MOVED TO R1
                              522
0216 B901                     523 DBCD:   MOV    AEX, #1         ; 2 BYTES
0218 B826                     524         MOV    R0, #BCD0       ; FIRST 2 DIGITS IN BCD
021A A9                       525         MOV    R1, A           ; DTBL, DTBL+4, DTBL+8
021B A5                       526         CLR    F1              ; F1=1 FOR BCD
021C B5                       527         CPL    F1
021D 4420                     528         JMP    DISP
                              529
                              530 ; BASIC DTBL SEGMENT LOADING ROUTINE
                              531
021F CA                       532 NCHAR:  DEC    AEX             ; DEC BYTE COUNT
0220 543B                     533 DISP:   CALL   GCHARS          ; A=CHAR/DIGIT PAIR
0222 47                       534         SWAP   A               ; MS NIBBLE
0223 542E                     535         CALL   G2SEG
0225 543B                     536         CALL   GCHARS
0227 542E                     537         CALL   G2SEG
0229 18                       538         INC    R0              ; NEXT CHAR PAIR
022A FA                       539         MOV    A, AEX          ; BYTE COUNTER
022B 961F                     540         JNZ    NCHAR           ; DONE YET?
022D 83                       541         RET
                              542
                              543 ; GET THE COMPLEMENTED SEGMENTS AND STORE IN DTBL
                              544 ; BCD SEGMENT TABLE MUST START AT 300H
                              545
022E 530F                     546 G2SEG:  ANL    A, #0FH         ; LS NIBBLE ONLY
0230 7634                     547         JF1    BCDSG           ; BRANCH IF BCD
```

MDS-II MCS-48/UPI-41 MACRO ASSEMBLER, V2.0                     PAGE   11
SM-410 BP9.LST REV 0 06/12/79 PROM 43

LOC  OBJ           SEQ          SOURCE STATEMENT

```
0232 0310                     548         ADD    A, #APHSEG-BCDSEG      ; ALPHA SEG TBL
0234 E3                       549 BCDSG:  MOVP3  A, @A            ; GET THE SEGMENTS
0235 37                       550         CPL    A                ; COMPLEMENT SEGMENTS
0236 537F                     551         ANL    A, #7FH          ; MASK PULSE BIT
0238 A1                       552         MOV    @R1, A           ; STORE IN DTBL
0239 19                       553         INC    R1               ; NEXT DTBL LOCATION
023A 83                       554         RET
                              555
                              556 ; GET THE CHAR/DIGIT PAIR AND LOAD INTO ACC
                              557
023B 7640                     558 GCHARS: JF1    BCHAR            ; BRANCH IF BCD
023D F8                       559         MOV    A, R0            ; R0=PAGE 3 TBL LOCATION
023E E3                       560         MOVP3  A, @A
023F 83                       561         RET
0240 F0                       562 BCHAR:  MOV    A, @R0           ; R0=BCD0, BCD1
0241 83                       563         RET
                              564
                              565 ; DISPLAY NEXT CHAR/DIGIT ON 12 CHAR LED DISPLAY
                              566 ; ROUTINE RUNS USING REGISTER BANK 1
                              567
0242 0A                       568 SEGS:   IN     A, P2            ; DIG # FROM PORT 2
0243 37                       569         CPL    A
0244 47                       570         SWAP   A                ; INTO LS NIBBLE
```

```
0245 17        571        INC    A              ; NEXT DIGIT #
0246 530F      572        ANL    A, #0FH        ; LS NIBBLE ONLY
0248 A9        573        MOV    DIGSAV, A      ; SAVE NEXT DIG #
0249 964F      574        JNZ    NXTINV         ; RESET SEGPTR IF DGT=0
024B B834      575        MOV    SEGPTR, #DTBL
024D 445B      576        JMP    INCDIG         ; MUST INC DIGIT
024F 03FE      577 NXTINV: ADD   A, -#02H       ; DIGIT=2 INVALID
0251 C65B      578        JZ     INCDIG
0253 03FE      579        ADD    A, -#02H       ; DIGIT=4 INVALID
0255 C65B      580        JZ     INCDIG
0257 03FB      581        ADD    A, -#05H       ; DIGIT=9 INVALID
0259 965D      582        JNZ    SEGOUT
025B 19        583 INCDIG: INC   DIGSAV         ; INC DIGIT #
025C F9        584 SEGOUT: MOV   A, DIGSAV      ; GET DIG #
025D 47        585        SWAP   A              ; PUT IN MS NIBBLE
025E 37        586        CPL    A
025F 53F7      587        ANL    A, #0F7H       ; VALVE CLOSE = 0
0261 A9        588        MOV    DIGSAV, A      ; SAVE DIGIT
0262 0A        589        IN     A, P2          ; GET VALVE CLOSE BIT
0263 5308      590        ANL    A, #08H
0265 49        591        ORL    A, DIGSAV      ; FORM P2 BYTE
0266 897F      592        ORL    P1, #07FH      ; BLANK DISPLAY
0268 3A        593        OUTL   P2, A          ; NEW DIG #
0269 09        594        IN     A, P1          ; GET PULSE BIT
026A 5380      595        ANL    A, #80H
026C 40        596        ORL    A, @SEGPTR     ; GET COMP SEGMENTS
026D 39        597        OUTL   P1, A          ; OUTPUT SEGMENTS
026E 18        598        INC    SEGPTR         ; NEXT CHAR SEGMENTS
026F 83        599        RET
              600
              601 ; WHEN USING SUBTRACT ROUTINES FOR COMPARISON,
              602 ;       X > Y: CARRY = 1
```

ISIS-II MCS-48/UPI-41 MACRO ASSEMBLER, V2.0    PAGE   12
M-410 BP9.LST REV 0 06/12/79 PROM 43

LOC  OBJ       SEQ        SOURCE STATEMENT

```
              603 ;        X = Y: A = 0, CARRY = 1
              604 ;        X < Y: CARRY = 0
              605
              606 ; DOUBLE PRECISION SUBTRACT:
              607 ;        DMINV: X (R0) - Y (R1)
              608 ;        DMINC: X (R0) - 1 (AEX, A)
              609 ; DOUBLE PRECISION ADDITION:
              610 ;        DADDC: X (R0) + K (AEX, A)
              611
0270 F1       612 DMINV:  MOV    A, @R1         ; LS BYTE
0271 AA       613        MOV    AEX, A         ; SAVE IN AEX
0272 19       614        INC    R1             ; MS BYTE
0273 F1       615        MOV    A, @R1
0274 2A       616        XCH    A, AEX         ; A=LSB, AEX=MSB
0275 C9       617        DEC    R1             ; RESTORE R1 PTR
0276 37       618 DMINC:  CPL    A              ; 1'S COMPLEMENT
0277 2A       619        XCH    A, AEX
0278 37       620        CPL    A
0279 2A       621        XCH    A, AEX
027A 97       622        CLR    C              ; SET CARRY
027B A7       623        CPL    C
027C 447F     624        JMP    DADDC1
027E 97       625 DADDC:  CLR    C
027F 70       626 DADDC1: ADDC   A, @R0         ; 2'S COMP ADDITION
0280 2A       627        XCH    A, AEX
0281 18       628        INC    R0
0282 70       629        ADDC   A, @R0
0283 2A       630        XCH    A, AEX         ; A=LSB, AEX=MSB
0284 C8       631        DEC    R0             ; RESTORE R0 PTR
0285 83       632        RET
              633
              634 ; BINARY TO BCD CONVERSION: RESULT IN BCD0, BCD1; X (R0)
              635
0286 B926    636 BINBC1: MOV    R1, #BCD0      ; VARIABLE TO BCD0
0288 74EC    637        CALL   DMOVE
028A 4499    638        JMP    BIN1
028C B926    639 BINBCD: MOV    R1, #BCD0      ; VARIABLE TO BCD0
              640
```

```
                641 ; DIVIDE BY 2, DOUBLE PRECISION RIGHT SHIFT
                642
028E 18         643         INC     P0              ; NEED MS BYTES
028F 19         644         INC     P1
0290 97         645         CLR     C
0291 F0         646         MOV     A, @P0          ; "FROM"
0292 67         647         RRC     A
0293 A1         648         MOV     @P1, A          ; "TO"
0294 C8         649         DEC     P0              ; LS BYTES
0295 C9         650         DEC     P1
0296 F0         651         MOV     A, @P0          ; "FROM"
0297 67         652         RRC     A
0298 A1         653         MOV     @P1, A
                654
                655 ; CONVERSION
                656
0299 B900       657 BIN1:   MOV     R1, #0          ; ACCUMULATE 100'S DIGIT
```

ISIS-II MCS-48/UPI-41 MACRO ASSEMBLER, V2.0                    PAGE   13
ESM-410 BP9.LST REV 0 06/12/79 FROM 43

LOC  OBJ         SEQ         SOURCE STATEMENT

```
029B BA00       658 HNDS:   MOV     REX, #0         ; 100 IN REX, A
029D 2364       659         MOV     A, #100
029F B826       660         MOV     P0, #BCD0
02A1 5476       661         CALL    D1INC           ; BCD# - 100
02A3 E6AA       662         JNC     LT100           ; BRANCH IF BCD#-100<100
02A5 19         663         INC     R1              ; INC 100'S COUNTER
02A6 54E9       664         CALL    DST             ; BCD# = BCD# - 100
02A8 449B       665         JMP     HNDS            ; SUBTRACT 100 AGAIN
02AA F9         666 LT100:  MOV     A, R1           ; MS DIGIT TO BCD0
02AB B900       667         MOV     R1, #0          ; ACCUMULATE TEN'S DIGIT
02AD 43F0       668         ORL     A, #0F0H        ; BLANK LEADING 0
02AF B826       669         MOV     P0, #BCD0
02B1 20         670         XCH     A, @P0          ; GET BCD0, < 100
02B2 AA         671 TENS:   MOV     REX, A          ; SAVE 10'S VALUE IN REX
02B3 03F6       672         ADD     A, -#10         ; SUBTRACT 10
02B5 E6BA       673         JNC     LT10            ; BRANCH IF REMAINDER<10
02B7 19         674         INC     R1              ; INCREMENT 10'S COUNT
02B8 44B2       675         JMP     TENS            ; SUBTRACT 10 AGAIN
02BA F9         676 LT10:   MOV     A, R1           ; GET TEN'S
02BB 47         677         SWAP    A               ; TEN'S TO MS NIBBLE
02BC 4A         678         ORL     A, REX          ; UNIT'S TO LS NIBBLE
02BD 18         679         INC     P0              ; POINT TO BCD1
02BE A0         680         MOV     @P0, A          ; TEN'S, UNIT'S TO BCD1
02BF 83         681         RET
                682
                683 ; BLINK MESSAGE ON DISPLAY
                684
02C0 54C4       685 BLINK:  CALL    BLINK1          ; MESSAGE ON DISPLAY
02C2 232D       686         MOV     A, #BLANK-PG3   ; BLANK DISPLAY
02C4 5408       687 BLINK1: CALL    DALFHA
02C6 2303       688         MOV     A, #3
02C8 44F2       689         JMP     WAIT
                690
                691 ; CHECK IF BATTERY IS BELOW SYSTEM OPERABLE LIMITS
                692
02CA 0A         693 BDEHD:  IN      A, P2
02CB 52D3       694         JB2     BEXIT           ; BRANCH IF BATT OK
02CD 2325       695 DSPDED: MOV     A, #CHARGE-PG3  ; "CH DC"
02CF 54C0       696         CALL    BLINK
02D1 44CD       697         JMP     DSPDED
02D3 83         698 BEXIT:  RET
                699
                700 ; SHIFT UP'S FOR PULSE AMPLITUDE
                701
02D4 BA03       702 SHFTH:  MOV     REX, #3         ; 3 SHIFTS
02D6 B829       703         MOV     P0, #HTBL+1     ; "FROM"
02D8 B928       704         MOV     P1, #HTBL       ; "TO"
02DA 54E2       705         CALL    SHFT1
                706
                707 ; SHIFT UP'S FOR PRESSURE
                708
02DC BA06       709 SHFTP:  MOV     REX, #6         ; 6 SHIFTS
02DE B82E       710         MOV     P0, #PTBL+2     ; "FROM"
02E0 B92D       711         MOV     P1, #PTBL       ; "TO"
                712
```

```
ISIS-II MCS-48/UPI-41 MACRO ASSEMBLER, V2.0                    PAGE   14
M-410 BP9.LST REV 0 06/12/79 PROM 43

LOC  OBJ          SEQ        SOURCE STATEMENT

713 ; SHIFT SUBROUTINE
                  714
02E2 F0           715 SHFT1:  MOV    A, @R0           ; "FROM"
02E3 A1           716         MOV    @R1, A           ; "TO"
02E4 18           717         INC    R0
02E5 19           718         INC    R1
02E6 EAE2         719         DJNZ   AEX, SHFT1
02E8 83           720         RET
                  721
                  722 ; DOUBLE PRECISION STORE: X (R0) = AEX, A
                  723
02E9 A0           724 DST:    MOV    @R0, A           ; LS BYTE
02EA 2A           725         XCH    A, AEX           ; MS BYTE
02EB 18           726         INC    R0
02EC A0           727         MOV    @R0, A
02ED 2A           728         XCH    A, AEX           ; RESTORE AEX, A
02EE C8           729         DEC    R0               ; RESTORE R0
02EF 83           730         RET
                  731
                  732 ; DELAY 100 MSEC INCREMENTS, # IN ACC
                  733
02F0 230A         734 M1SEC:  MOV    A, #10           ; 1 SEC DELAY
02F2 B81E         735 WAIT:   MOV    R0, #0X22
02F4 A0           736         MOV    @R0, A
02F5 F0           737 WT:     MOV    A, @R0
02F6 96F5         738         JNZ    WT
02F8 83           739         RET
                  740
                  741 ; SEGMENT TABLES: MUST BE AT BEGINNING OF PAGE 3
                  742
0300              743         ORG    PG3
                  744
0300 3F           745 BLDSEG: DB     3FH, 06H, 5BH, 4FH, 66H, 6DH, 7DH, 07H
0301 06
0302 5B
0303 4F
0304 66
0305 6D
0306 7D
0307 07
0308 7F           746         DB     7FH, 67H, 77H, 7CH, 39H, 5EH, 40H, 0
0309 67
030A 77
030B 7C
030C 39
030D 5E
030E 40
030F 00
                  747
0310 77           748 AP1SEG: DB     77H, 39H, 5EH, 79H, 76H, 06H, 3EH, 38H
0311 39
0312 5E
0313 79
0314 76
0315 06
```

```
ISIS-II MCS-48/UPI-41 MACRO ASSEMBLER, V2.0                    PAGE   15
ISM-410 BP9.LST REV 0 06/12/79 PROM 43

LOC  OBJ          SEQ        SOURCE STATEMENT 0316 3E
0317 38
0318 71           749         DB     71H, 3FH, 5CH, 73H, 50H, 6DH, 6EH, 00H
0319 3F
031A 5C
031B 73
031C 50
031D 6D
031E 6E
031F 00
```

```
                              750
                              751 ; MESSAGES
                              752
0320 FD                       753 SYSERR: DB      0FDH, 0EDH
0321 ED
0322 F3                       754 PERPUR: DB      0F3H, 0CCH, 0ACH
0323 CC
0324 AC
0325 FF                       755 CHARGE: DB      0FFH, 0FFH, 0FFH, 0F1H, 4FH, 21H
0326 FF
0327 FF
0328 F1
0329 4F
032A 21
032B 10                       756 CAL:    DB      10H, 7FH
032C 7F
032D FF                       757 BLANK:  DB      0FFH, 0FFH
032E FF
032F FF                       758 CUFF:   DB      0FFH, 0FFH, 0FFH, 0FFH, 16H, 88H
0330 FF
0331 FF
0332 FF
0333 16
0334 88
0335 F2                       759 DIHERR: DB      0F2H, 50H, 0F3H, 0CCH, 0ACH
0336 50
0337 F3
0338 CC
0339 AC
033A FF                       760 LOBATT: DB      0FFH, 0FFH, 0FFH, 0F7H, 9FH, 21H
033B FF
033C FF
033D F7
033E 9F
033F 21
0340 79                       761 LOCCPR: DB      79H, 0F9H, 11H, 0FBH, 0C3H, 0DDH
0341 F9
0342 11
0343 FB
0344 C3
0345 DD
0346 45                       762 HOCCPR: DB      45H, 0F9H, 11H
0347 F9
0348 11
0349 FB                       763 PRESS:  DB      0FBH, 0C3H, 0DDH, 0FFH
```

ISIS-II MCS-48/UPI-41 MACRO ASSEMBLER, V2.0                    PAGE   16
SM-410 BP9.LST REV 0 06/12/79 PROM 43

LOC  OBJ         SEQ         SOURCE STATEMENT

```
034A C3
034B DD
034C FF
034D FF                       764 OCCL:   DB      0FFH, 0FFH, 0F9H, 11H, 76H, 23H
034E FF
034F F9
0350 11
0351 76
0352 23
                              765
                              766 ; SUBROUTINES - MORE
                              767
                              768 ; PULSE DETECT
                              769
0353 54CA                     770 PLS:    CALL    BPEND           ; CHECK BATTERY
0355 5404                     771         CALL    SHFTH           ; MOVE H'S, PR'S UP 1
0357 85                       772 PLS1:   CLR     F0              ; CLEAR PULSE FLAG
0358 B824                     773         MOV     R0, #PTMP
035A B932                     774         MOV     R1, #PLAST
035C 74BC                     775         CALL    DMOVE           ; PLAST=PTMP
035E B82B                     776         MOV     R0, #H0         ; INITIAL HEIGHT = 0
0360 B000                     777         MOV     @R0, #0
0362 74FA                     778 S1LAST: CALL    READP           ; READ PRESSURE, PTMP
0364 2330                     779         MOV     A, #30+2        ; PRESS < 30?
```

```
0366 BA00       780        MOV    REX, #0
0368 5476       781        CALL   DMINC
036A F678       782        JB7    ST1                   ; BRANCH IF >= 30
036C FD         783        MOV    A, PLSCNT             ; CHECK FOR 4 PULSES
036D 03FD       784        ADD    A, -#3
036F 37         785        CPL    A                     ; NEED COMP OF MSB
0370 F274       786        JB7    DIHER                 ; > 4 PULSES?
0372 2401       787        JMP    SYSER                 ; "SYS ERROR"
0374 2325  788 DIHER: MOV  A, #DIAERR-PG3               ; "DIA ERROR"
0376 2403       789        JMP    DPECAL
0378 B922  790 ST1:   MOV  R1, #PLAST                   ; COMPARE PTMP AND PLAST
037A 5470       791        CALL   DMINV                 ; H=PTMP-PLAST<256
037C B81C       792        MOV    R0, #HUX33            ; PULSE WIDTH TIMER
037E B92B       793        MOV    R1, #HD               ; SET UP FOR AMP CHK
0380 F68F       794        JNC    PCHKS                 ; BRANCH IF PTMP < PLAST
0382 AA         795        MOV    REX, A                ; SAVE H IN REX
0383 F1         796        MOV    A, @R1                ; COMPARE H WITH HD
0384 37         797        CPL    A
0385 17         798        INC    A
0386 6A         799        ADD    A, REX
0387 F262       800        JB7    STLAST                ; H<HD, NEXT READING
0389 FA         801        MOV    A, REX                ; HD = H
038A A1         802        MOV    @R1, A                ; HD = H
038B 03FE       803        ADD    A, -#2                ; AMPL THRESHOLD=1.0 MM
038D F262       804        JB7    STLAST
                805
                806 ; PULSE WIDTH TIMER SET UP
                807
038F B494       808        JMP    AUXCHK
0391 95         809        CPL    F0                    ; SET FOR PULSE ONSET
0392 B04B       810        MOV    @R0, #75              ; 60 MSEC
```

ISIS-II MCS-48/UPI-41 MACRO ASSEMBLER, V2.0        PAGE 17
LSM-410 BP9.LST REV 0 06/12/79 PROM 43

LOC  OBJ        SEQ        SOURCE STATEMENT

```
0394 F0    811 AUXCHK: MOV  A, @R0
0395 9662       812        JNZ    STLAST
                813
                814 ; VALID PULSE- TURN ON LITE, CHECK MAX AMPLITUDE
                815
0397 997F       816        ANL    P1, #7FH              ; PLS LITE ON
0399 23F0       817        MOV    A, -#&2               ; MAX PULSE AMPL
039B 61         818        ADD    A, @R1
039C E662       819        JNC    STLAST
039E 2322       820        MOV    A, #PERROR-PG3        ; "ERROR"
03A0 2403       821        JMP    DPECAL
                822
                823 ; VALID PULSE WIDTH CHECK
                824
03A2 09    825 PCHKS: IN     A, P1                      ; VALID PULSE WIDTH?
03A3 37         826        CPL    A                     ; BIT 7 IS PLS LITE
03A4 F2C1       827        JB7    PCHKS1                ; BRANCH IF YES
                828
                829 ; NO PULSE, DECREASING OCCLUDING PRESSURE
                830
03A6 5410       831        CALL   PSPRES
03A8 B91E       832        MOV    R1, #HUX22            ; TIME UP YET?
03AA F1         833        MOV    A, @R1
03AB 9657       834        JNZ    PLS1                  ; BRANCH IF NOT
03AD FF         835        MOV    A, TENSEC             ; TEN SEC UP?
03AE 96B9       836        JNZ    PVALID
03B0 FD         837        MOV    A, PLSCNT             ; ANY PULSES YET?
03B1 F257       838        JB7    PLS1
03B3 BFFF       839        MOV    TENSEC, #0FFH         ; TEN SEC UP
03B5 B11E       840        MOV    @R1, #30              ; 3 SEC TIMEOUT
03B7 6457       841        JMP    PLS1
03B9 FE    842 PVALID: MOV   A, PLSVLD                  ; VALID PULSE COUNT?
03BA 9674       843        JNZ    DIHER                 ; NO PULSE FOR 3 SEC
03BC BC00       844        MOV    PLSCNT, #0
03BE BEFF       845        MOV    PLSVLD, #0FFH
03C0 83         846        RET
                847
```

```
                   848 ; CURRENT PULSE AMPLITUDE: CANNOT BE 1 MM HG LARGER
                   849 ;     THAN PREVIOUS PULSE
                   850
03D1 8980          851 PLUKS1: ORL     P1, #80H            ; PLS LITE OFF
03D3 B82A          852         MOV     R0, #H3
03D5 F0            853         MOV     A, @R0              ; A=H3
03D6 0302          854         ADD     A, #2               ; A=H3+2
03D8 AA            855         MOV     REX, A              ; SAVE H3+2
03D9 37            856         CPL     A
03DA 17            857         INC     A
03DB 61            858         ADD     A, @P1              ; H4-(H2+2)
03DC F6D0          859         JNC     WINDOW              ; BRANCH IF H4<H3+2
03DE FA            860         MOV     A, REX              ; H4=H3+2
03DF A1            861         MOV     @P1, A
                   862
                   863 ; SET UP TEN SECOND PULSE COUNT WINDOW
                   864
03E0 FC            865 WINDOW: MOV     A, PLSCNT           ; PLS COUNT = 0?
```

IS-II MCS-48/UPI-41 MACRO ASSEMBLER, V2.0                         PAGE   18
SM-410 BP9.LST REV 0 06/12/79 FROM 43

LOC  OBJ           SEQ              SOURCE STATEMENT

```
03E1 96E4          866         JNZ     TFGCHK
03E3 B91D          867         MOV     P1, #0CC11          ; SET UP 10 SEC TIMER
03E5 B17D          868         MOV     @P1, #125           ; 100 MSEC
03E7 19            869         INC     P1                  ; 10 SECONDS
03E8 B164          870         MOV     @P1, #100
                   871
                   872 ; PULSE COUNT
                   873
03EA B91E          874 TFGCHK: MOV     P1, #0CC22          ; SEC COUNTER
03EC FF            875         MOV     A, TENSEC           ; 10 SEC UP?
03ED 96E5          876         JNZ     TENUP               ; BRANCH IF > 10
03EF F1            877         MOV     A, @P1              ; 10 SEC CHECK
03E0 C6E5          878         JZ      TENUP               ; BRANCH IF 10 SEC UP
03E2 10            879         INC     PLSCNT              ; ONE MORE PULSE
03E3 64EB          880         JMP     PEXIT
03E5 BEFF          881 TENUP:  MOV     PLSVLD, #0FFH       ; VALID PULSE COUNT
03E7 BFFF          882         MOV     TENSEC, #0FFH       ; 10 SECONDS UP
03E9 B11E          883         MOV     @R1, #30            ; 3 SEC TIME OUT
                   884
                   885 ; PULSE AMPLITUDE TESTING
                   886
                   887         IF      TEST EQ TRUE
                   888
                   889 PEXIT:  MOV     P1, #HD             ; GET AMPLITUDE
                   890         MOV     A, @P1
                   891         MOV     P1, #DTBL+7         ; DISPLAY POSITION
                   892         JMP     BCDSG               ; DISPLAY PLS AMPL
                   893
                   894         ELSE
                   895
03EB 83            896 PEXIT:  RET
                   897
                   898         ENDIF
                   899
                   900 ; DOUBLE MOVE: R0 = "FROM" ADDRESS, R1 = "TO" ADDRESS
                   901
03EC F0            902 DMOVE:  MOV     A, @R0              ; "FROM"
03ED A1            903         MOV     @P1, A              ; "TO"
03EE 18            904         INC     R0
03EF 19            905         INC     P1
03F0 F0            906         MOV     A, @R0              ; FROM, MS BYTE
03F1 A1            907         MOV     @P1, A              ; TO, MS BYTE
03F2 C8            908         DEC     R0                  ; RESTORE PTRS
03F3 C9            909         DEC     R1
03F4 83            910         RET
                   911
```

Sequencing of the Apparatus

Before proceeding with a description of the source listing and the detailed steps carried out by the apparatus of FIGS. 1-8, it will be helpful to summarize the sequencing of the instrument.

After the occluding cuff is placed on the arm of the patient in the conventional manner, the main on/off switch is moved to the on position, and the system is reset by momentarily depressing the reset switch. The "CAL" message is then displayed for at least two seconds while the system checks that the cuff pressure is at atmospheric pressure and while the reference pressure is measured. The "CAL" message may be displayed for more than two seconds if the cuff pressure has to bleed down (e.g., if the instrument was just used, and a new measurement cycle was initiated by pressing the reset button before the cuff pressure was allowed to completely bleed down at the end of the previous measurement cycle).

The "CUFF" message is then normally displayed to inform the operator to press the recall/cuff button. Alternatively, if the battery potential is less than 9.8 volts, but higher than 9.4 volts, the "LO dC" message is displayed to inform the operator not only to press the recall/cuff button, but also to recharge the batteries when time permits. If the battery potential is detected to be less than 9.4 volts, either now or subsequently, a blinking "CH dC" message is displayed to inform the operator that the unit may not be used until the batteries are recharged.

As soon as the recall/cuff button is momentarily operated, the "OCCLUdE" message is displayed. The operator is thus informed to start pumping the bulb. If the operator starts to pump the bulb before pressing the recall/cuff button, the "CUFF" message will blink. In such a case, the reset switch must be operated and the whole process started from the beginning.

The "OCCLUdE" message remains on the display as the pumping proceeds until a pressure of 40 mm Hg is present in the cuff. At this time, the "PrESS" (pressure) message is displayed together with the instantaneous cuff pressure.

When the occluding pressure in the cuff exceeds 250 mm HG, the "HI OCC PrESS" message is displayed without a pressure value. The operator can still pump up the bulb, although generally this is not necessary.

If the operator has not pumped the bulb for 2.5 seconds, yet a blood pressure pulse representing a rise of at least 1.0 mm Hg was nevertheless detected by the instrument, it is an indication that the artery was not fully occluded (as will be explained below). The "LO OCC PrESS" message is displayed to inform the operator to pump up the cuff pressure.

Provided that 2.5 seconds go by after the operator stops pumping the bulb without the detection of a pulse having an amplitude of at least 1.0 mm Hg, the system begins to take systolic and diastolic pressure measurements, along with a measurement of pulse rate. As the occluding pressure bleeds down, the message "PrESS" is displayed, together with the decreasing cuff pressure value. Although each blood pressure pulse results in an instantaneous rise and then fall of cuff pressure, these transient changes are not displayed. The cuff pressure value which is displayed during the measurement cycle continuously decreases. However, whenever a blood pressure pulse is in progress, the pulse light is illuminated.

During the measurement cycle, artifacts may result in the display of an "Error" message. An error during systolic pressure processing results in the display of a "SYS Error" message, and an error during diastolic pressure processing results in the display of a "dIA Error" message. In all three cases, no measurement results are displayed, and the reset button must be operated to initialize the system for taking a new measurement.

At the conclusion of the measurement cycle, systolic pressure, diastolic pressure and pulse rate are displayed. If the pulse rate determination is too low or too high, indicating that an error probably occurred, the systolic and diastolic pressure values are displayed, but instead of a 3-digit pulse rate value being shown three dashes are displayed.

The final results (an error message or numerical values) are displayed for ten seconds. The display is then blanked, but the pulse light turns on to indicate to the operator that the last display can be recalled by pressing the recall/cuff button. If the button is operated, the pulse light turns off and the last message will be displayed for another ten seconds, following which it will be blanked and the pulse light will turn on again.

Another measurement cycle then can be initiated by pressing the reset button.

Organization of Data Memory and Display Procedure

Statements 9-72 define various labels used in the source program. At lines 9-11, TRUE is set equal to OFFH, and FALSE and TEST are both set equal to 0. Of the eight registers in bank 0, R0 and R1 are used as general pointers and are not provided with any labels. Registers R2-R7 are assigned labels which correspond to the respective information which they contain.

Six of the registers in bank 1 are similarly given labels. Registers R2 and R3 in this bank are used to store a double-precision reference pressure.

Starting with statement 39, some of the other locations in the 64-location data memory are provided with labels. Additionally, some of the bank 0 and bank 1 registers are given alternate labels. For example, in line 28, the label SEGPTR is assigned to register R0 in bank 1. Yet line 39 refers to this same register as SGPTR. The reason for this is that different labels are required when running the 8048 microprocessor working with the two different register banks. Label SEGPTR is used when running the machine with bank 1. The actual value of SEGPTR is 0, since the first working register in bank 1 (R0') is register 0 for that bank. But when running the processor with bank 0, the first register in bank 1 is referred to by its RAM address 24. Thus the label SGPTR actually has a value of 24.

At line 41, data memory locations 26 and 27 (registers R2 and R3 in bank 1) are defined as storing a double-precision (16-bit) reference pressure. The label PREF refers to the first of these two locations. (In general, in the following description, a label such as PREF is used loosely to refer either to the data memory location which contains the first, least significant byte of the 16-bit value or to the 16-bit value itself, depending on the context in which the label is used.)

Line 52 sets aside four data memory locations for storing pulse heights. The first of these is labeled HTBL and the last, as defined by line 53, is labeled HD. The eight locations starting at data memory address 54 are used to store four double-precision variables which represent pressure values. The last two of these locations store the "last" value, with the first location of these two being labeled PLAST. Lines 63-68 define alternate labels for the pressure value locations.

Statement 56 reserves the last 12 data memory locations (52-63) for a "display table" with location 52 being labeled DTBL. The display contains 12 character positions, some of which are blanks for particular messages. Every 800 microseconds, a different character is refreshed or newly displayed under timer interrupt control. The system does not then determine the current message which is being displayed, retrieve the character which is to be refreshed in that message, access the display segment information for that character, and finally use the segment information to control refreshing of the character (or the display of a new character if a message is to be changed). Rather, whenever an entirely new, or part of a, message is required (alphabet characters or digit characters), the system retrieves all of the new characters, and for each of the new characters derives display segment information. A single byte defines those segments for each character which are to be turned on, and those which are to be left off. The segment-controlling bytes are then stored in respective ones of data memory locations 52-63. (When an entirely new message is to be displayed, 12 bytes are stored in the display table; otherwise, only bytes corresponding to digit characters to be up-dated are stored in the display table.) Thereafter, at 800-microsecond intervals, a different one of these twelve data memory locations is accessed, and the respective character position of the display is refreshed or up-dated in accordance with the stored segment information. Each character is thus turned on at intervals of 12×800 microseconds, or 9.6 milliseconds, a rate high enough to avoid flicker, thus giving the appearance of a continuously illuminated display.

The last definitional statement, at line 72, is that which defines PG3 as ROM address 300H, the start of the fourth page of program memory. At this point, it will be helpful to refer to source statement lines 741-764. The 16 bytes stored starting at ROM address 300H (BCDSEG) represent display segment bits for the ten digits 0-9, four HEX digits A, b, C, d, a dash (minus sign), and a blank. (As will be described below, the HEX digits are displayed only in a testing mode—not by an instrument used by a purchaser. There are 16 alphabet characters—A, C, d, E, F, H, I, L, o, O, P, r, S, U, Y, and a blank, which are used to make up all of the messages, and display segment bit information for these 16 characters are stored starting at ROM address 310H (APHSEG).

The word messages themselves are defined in lines 753-764. Each byte represents two characters of a message. For example, consider the message "SYSERR" defined at line 753. The first byte of the message is FDH; the 4-bit HEX value F represents a blank (b) and the 4-bit HEX value D represents the letter S. The first six bytes starting at ROM address 320H represent the following pairs of characters, where a b represents a blank: bS, YS, bE, rr, or, bb. The four bits used to represent each character have no predetermined relationship with the character; each 4-bit value is simply an offset which is used to retrieve the respective segment information, as will be described below.

The "PERROR" message overlaps the "SYSERR" message, the former message beginning at ROM address 322H. The six bytes used to define this message represent the character pairs bE, rr, or, bb, bb, bb. Similarly, the "CHARGE" message overlaps the "PERROR" message and begins at location 325H. The character pairs represent bb, bb, bb, bC, Hb, dC. Similar remarks apply to all of the other messages.

Suppose, for example, that it is necessary to display the "CHARGE" message. The processor retrieves the 12 respective HEX digits FFFFFFF14F21. The first HEX digit is used as an offset and added to base address APHSEG (line 748, ROM address 310H). The display segment byte which is thus pointed to is that at ROM address 310H+FH, or 31FH. This byte (00) is stored in the first location DTBL of the display table, having data memory address 52. When the two HEX digits 00 are stored in this location of the data memory, the first character of the display is blanked. Because each of the next six HEX digits in the "CHARGE" message is also an F, the display segment bytes which are stored in data memory locations 53-58 are also 00 and control the display of blanks.

The next HEX digit in the "CHARGE" message is 1, and when this offset is added to APHSEG, ROM address 311H is pointed to. The HEX byte 39 at this location is thus stored at location 59 in the data memory, and it controls the display of a C in the eighth character position of the display. In a similar manner, the last four HEX digits of the "CHARGE" message—4, F, 2 and 1—are used as offsets from address APHSEG to access the four bytes which are segment information for the characters H, b (blank), d and C. These bytes are stored in the last four locations in the display table. Once the segment data is thus stored, up-dating of the display is automatic, with a different display segment byte being retrieved from the data memory every 800 microseconds and used to control the character display "CH dC".

When digit characters are to be displayed, a similar procedure is followed. But this time each computed digit is used as an offset to point to a display segment byte starting at base address BCDSEG (line 745). Once a byte of segment information is stored in one of the twelve positions of the display table in the data memory, display of the respective digit is automatic.

This technique requires the processor to "form" a message, or up-date it with new digit values, only once, by storing the appropriate display segment bytes in the data memory. Thereafter, the processor need not form the message, and must only change or refresh the display in accordance with the display segment information in the data memory.

It should be noted that the overlapping of the alphabet character messages (lines 753-764), as described above, results in some of the messages being displayed on the left, some in the middle, and some on the right of the display. The reason for doing this is simply to conserve ROM address space. By overlapping the messages, some of the same offset HEX digits can be used to represent characters in up to three messages. The necessary result of this ROM conservation is that the messages are actually displayed starting at different positions in the 12-position display.

Start-up of Machine, Timer Interrupt and Message Display

Following closing of the main on/off switch, the reset button is operated. The $\overline{\text{RESET}}$ input of the 8048 microprocessor is pulsed high. At the trailing edge of the pulse, the program counter is automatically loaded with address 0, the origin of the ROM program. When a 6-MHz crystal is used to derive the clock, a 400-kHz machine cycle clock is generated internally. This latter clock waveform is passed through an internal ÷32 prescaler to apply a 12.5-kHz clock to the 8-bit timer/counter included on the chip. The timer is thus incremented every 80 microseconds. Initially, the timer/counter interrupt is not enabled and all that is done is to initialize the timer.

The first instruction (line 78) stores the decimal number −10 in the accumulator, and the next instruction transfers this number to the timer/counter. Register RO is then loaded with the value of SGPTR (24), which identifies the first register (RO') in register bank 1. The system then jumps to the SEGSET routine at line 116.

At line 116, register RO is loaded with the value 52 (DTBL), identifying the first of the 12 data memory locations used to store display segment information. During assembly, the assembler computes the value CAL-PG3, and generates an instruction at line 117 which causes this value to be loaded in the accumulator. CAL is the absolute address (32BH) in ROM of the start of the "CAL" (calibrate) message (see line 756). When the value PG3 (300H) is subtracted from the value CAL, the difference represents the relative address in page 3 of ROM at which the "CAL" message offsets begin.

At line 118, a call is made to the DALPHA subroutine at line 506. This routine is used repeatedly and will be described in detail.

The number 5 is first stored in the AEX register (R2, see line 17). This register is used to count operations on six bytes (12 offsets) of the message to be displayed, representing 12 characters. (In general, to change any part of a message, AEX is initially loaded with one less than the number of bytes, or double characters, to be processed.) The accumulator contains the relative address in page 3 of ROM of the first byte whose two characters are to be displayed. The MOV instruction in line 507 causes this relative address to be stored in register RO. When the next instruction is executed, the first display table location (DTBL) in the data memory which is to be changed is stored in register R1. Flag F1 is then cleared, as it is whenever alphabet character message segments are to be loaded into the display table, and a jump is made to the DISP routing at line 533.

A call is immediately made to the GCHARS subroutine at line 558. Since the F1 flag is cleared, a branch is not made to BCHAR. At line 559, the accumulator is loaded with the relative address in page 3 of the byte representing the first two characters of the "CAL" message (contained in register R0), and the MOVP3 instruction then causes the byte at this location to be moved to the accumulator. A return is then made to line 534.

The byte now in the accumulator represents the first two characters of the message. In order to operate on the four most significant bits of the byte, representing the first character, it is necessary to place this HEX digit in the four least significant bits of the accumulator; this is accomplished by the SWAP instruction at line 534. A call is then made to the G2SEG subroutine at line 546. By ANDing the accumulator with OFH, the four most significant bits in the accumulator are cleared. At line 547, a branch is not made to BCDSG because the F1 flag is cleared, since an alphabet character is to be displayed. The instruction at line 548 causes the relative address in page 3 of the first alphabet character segment byte to be added to the contents of the accumulator, and thus the accumulator represents the relative address in page 3 of the display segment byte associated with the first character to be displayed. At line 549, the display segment byte of interest is loaded into the accumulator, and at line 550 the accumulator is complemented. (The accumulator is complemented because all outputs of the microprocessor connected to the display are inverted by external inverters included for current amplification.)

The seven least significant bits of the accumulator represent display segment information for the character to be displayed. The most significant bit is used to illuminate the "pulse" light whenever a pulse detection is to be indicated. Whatever the value of the bit is at this time, it will be outputted again, but for the time being the most significant bit of the accumulator is cleared by the ANL instruction at line 551. The accumulator contents are then stored in the data memory location represented by register R1, namely, location 52 (DTBL)—the first in the display table. Register R1 is then incremented so that it points to the next location in the display table, and a return is made to the instruction at line 536.

A call is now made to the GCHARS routing once again. Since register R0 still represents the relative address in page 3 of the first two-character byte, the same two-character byte is stored in the accumulator and a return is made to line 537. This time, however, the two nibbles in the accumulator are not swapped because the second character to be displayed is represented in the four least significant bits. A call is made to the G2SEG subroutine which results in the segment byte for the second character being loaded in the next location in the display table, and register R1 is incremented so that it points to the third location in the display table.

At line 538, register R0 is incremented so that it points to the next byte (character pair) in the "CAL" message. A test is then made to see if six bytes (12 characters) have been processed. The contents of the AEX register are moved to the accumulator and, if the accumulator value is not zero, a jump is made to NCHAR (line 532). The value in the AEX memory location is decremented, and the DISP routine is executed once again. It is apparent that after 12 characters have been processed, the AEX value will be 0, and at line 541 a return will be made to line 119.

It should be noted that whenever DALPHA (line 506) is called, the F1 flag is cleared to represent that an alphabet character is to be displayed. Whenever digit values are to be displayed, as will be described below, the F1 flag is set and register R0 is loaded with the address BCD0, that is, the address of the location in data memory which contains the first two BCD digit offsets (or values, since each value is used as an offset to retrieve a segment byte). At line 547, a branch is made to line 549 (BCDSG) which simply results in the base relative address in page 3 for the digit segment bytes to be loaded in the accumulator, rather than the base relative address in page 3 for the alphabet character segment bytes. In this way, the same routine at line 549 can load digit segment bytes into the display table. Similarly, in the GCHARS subroutine at line 558, instead of loading the accumulator with a message character relative address, the branch at line 558 to line 562 causes the digits themselves (representing two offsets) to be loaded directly into the accumulator.

Referring back to line 116, it should be noted what is required to set up a new word message. Whenever a new message is to be displayed, the value DTBL is loaded into register R0, and the relative address in page 3 of the byte representing the first two characters is loaded into the accumulator. A call to DALPHA then results in storage in the data memory of the 12 display segment bytes for the message; the characters of the display are then refreshed automatically at 800-microsecond intervals as will be described below.

Thus far, however, the timer/counter has not been enabled. All that has been done is to store the number −10 in it (line 78). It is enabled at line 119, and at line 120 the timer counting is started. Since the number −10 is initially stored in the counter, the first timer interrupt occurs 800 microseconds after the timer is started.

The system proceeds to line 124, but it will be helpful at this point to digress and to consider what happens when a timer interrupt is generated. Timer interrupts, resulting from timer/counter overflows, always cause the program counter to be loaded with address 7 (line 87). The SEL RB1 instruction causes register bank 1 to be selected; it is this register bank which is used during the timer interrupt processing. The accumulator is saved in register R7' (ASAV) in this register bank so that after the refreshing of a display character, normal processing can resume. The timer is then enabled for another 800-microsecond cycle by loading −10 in the accumulator and moving it to the timer/counter.

A call is then made to the SEGS subroutine at line 568. Every 800 microseconds, a single display character is refreshed. But the system does not maintain a record of the last character position which was refreshed. The position is actually represented and latched at port 2, bits 4–7, and these bits are examined to determine the next character which is to be refreshed (or changed, if since the last refreshing the display table contents were changed). At line 568, the eight bits latched at port 2 are read into the accumulator. It is the complement of the four most significant bits which represent one of the twelve character positions due to the provision of the inverters at port 2. It is for this reason that the accumulator contents are complemented at line 569. Because the four most significant bits represent the last character position which was refreshed, the two nibbles in the accumulator are swapped at line 570, to place the complemented four most significant bits latched at the port in the four least significant bits of the acumulator. By incrementing the accumulator at line 571, the next character position is determined.

The accumulator is then ANDed with the HEX digits OF so that only the least significant nibble remains in the accumulator, and the accumulator contents are stored in DIGSIV at line 573.

The decoder/driver has four input bits, and 12 outputs extended to the cathodes of the 12 display elements. Thus four of the sixteen possible input codes do not result in the driving of a respective one of the 12 output lines. In the particular chip used, codes 0, 2, 4 and 9 are not used. The least significant nibble in the accumulator was previously incremented to represent the next character position to be processed. If the accumulator was incremented to 0 (from 16), representing an unused code, the test at line 574 does not result in a branch to line 577. Instead, the address of the first location in the display table is stored in SEGPTR since it is this data memory location which contains the segment byte to be used. A jump is then made to line 583 (INC-DIG). Since the first character position of the display is represented by the decoder code of 1, not 0, DIGSAV, which contains the number of the next character position to be refreshed, is incremented. Starting at line 584, the character position is refreshed, using the character code position in DIGSAV and the segment byte whose location is stored in SEGPTR. On the other hand, if the incremented code position in DIGSAV is not 0 at line 574, a test is made to see if it represents one of the three other invalid codes. At line 577, −2 is added to the accumulator. If the result is zero, indicating incrementing up to an invalid code of 2, a jump is made to line 583 where DIGSAV is incremented, following which the identified character position is refreshed. If the code position is not 2, then at line 579, −2 is added once again to the accumulator to see if the accumulator originally represented invalid code 4. If it did, a jump is made once again to line 583. Finally, by adding −5 to the accumulator at line 581, a test is made to see if the accumulator represented invalid code 9. If it did not, a jump is made directly to line 584; otherwise, DIGSAV is incremented, and only then is the SEGOUT routine executed.

Data memory location DIGSAV contains the character position to be operated upon in its four least significant bits, and its four most significant bits are 0. Because the character position is outputted at bits 4–7 of port 2, it is necessary to swap the two HEX digits stored in DIGSAV so that the position code is represented by the most significant nibble. At line 584, DIGSAV is placed in the accumulator, and the two nibbles are swapped at line 585. But the most significant bits of the accumulator now represent the actual position code, and due to the provision of the inverters at port 2, the actual code will be provided to the decoder/driver only if the complemented code is outputted at the port. For this reason, at line 586 the accumulator is complemented.

Referring to FIGS. 5 and 6, it will be noted that only four of the bits at port 2 control selection of a character position in the display. Bits 0, 1 and 2 are used as inputs, and when outputting a byte at port 2 it makes no difference which values are placed at the three pins used as inputs. But bit 3 of port 2 (pin 24 of the 8048 chip) is used as an output to control operation of the valve which opens the cuff to the atmosphere. Whatever the present value of this bit, it must not be changed when outputting a new character position for the decoder/driver.

At line 587, the accumulator contents are ANDed with the two HEX digits F7. This results in no change in all bits other than bit 3; this bit is cleared. The accumulator contents are then stored in DIGSAV. The routine now tests the value of bit 3 which is latched at port 2, and places this value in DIGSAV before outputting the byte at port 2. At line 589, the latched data bits at port 2 are loaded into the accumulator and at line 590 all of the bits are cleared except bit 3. This remaining bit is ORed with DIGSAV at line 591, and the new byte is outputted and latched at port 2 by the OUTL instruction at line 593.

But before this is actually done, an ORL instruction is executed at line 592. If the cathode of the new position in the display is energized while the seven least significant bits at port 1 still represent the respective states of the display segments for the previous character position, until the bit values at port 1 are actually changed the character represented at the position previously operated upon will actually be displayed at the new character position for a tiny fraction of a second, until a new display segment byte is outputted at port 1. To avoid this "bleeding" (which lasts for about 20 microseconds), all of the segment drivers are de-energized. They are de-energized only until a new cathode is selected, following which a new display segment byte is outputted at port 1.

There is one exception, however, and that relates to the most significant bit 7 at port 1. This bit is used to control the "pulse" light. Each digit or alphabet character requires the selective energization of seven segments, represented by the seven least significant bits in a respective location in the display table of the data memory. Other routines determine when the pulse light is to be illuminated, and when it is to be illuminated bit 7 of port 1 is forced low. Thus when causing the bit outputs at port 1 to go high momentarily to avoid "bleeding" (bit output of 1 turns off a respective display segment), the bit value at pin 34 (bit 7 of port 1) should not be changed. At line 592, the two HEX digits 7F are ORed with the output bits at port 1. There is no change in the latched value at bit 7 of the port, but all of the other seven bits are latched to the 1 state. The inverters at the port outputs cause 0's to be applied to the seven segment lines, while the previously applied value appears on the line extended to the pulse light. Thus the light remains off if it was off, or on if it was on, but all seven segment lines are driven low. Thus even though the cathode of the next character position is selected before the new segment values appear at port 1, no display appears at this character position.

At line 594, the latched outputs at port 1 are loaded into the accumulator. (As described immediately above, seven of these outputs are now 1's.) At line 595, all bits are cleared, except the most significant bit which remains as it was. Register R0' (SEGPTR) points to the address of the location in the display table which contains the segment byte to be outputted. At line 596, the display segment byte is ORed with the contents of the accumulator, so that the accumulator now represents the segments of the next character position which are to be energized, as well as a most significant bit which represents the state of the pulse light. The accumulator is then outputted at line 597 to port 1 to control both the pulse light and the refreshing of the new character position.

At line 598, SEGPTR is incremented so that it points to the next location in the display table (data memory locations 52–63). (SEGPTR is reset to the first location at line 575, as described above, whenever the first display position is to be operated upon.) At line 599, a return is made to the timer interrupt program at line 92.

It should be noted that because of the ORL instruction at line 596, a 1 may not be stored in bit 7 of any of the 12 locations in the display table. This would result in a 1 being outputted at bit 7 of port 1, and the permanent disablement of the pulse light. Consequently, a 0 must be stored in the most significant bit position in each of the 12 locations of the diaplay table, and it is an examination of the pulse light latched bit (port 1, bit 7) which is the sole control over whether the light is pulsed again. A 0 is stored in the most significant bit position of every byte in the display table by making bit 7 of every segment byte, for both alphabet characters and digits, a 0. The most significant bit in each of ROM locations 300H-31FH is therefore a 0.

At line 92, the contents of data memory location AUX3 are moved to the accumulator. If the value is 0, at line 93 a jump is made to line 95. Otherwise, the value in AUX3 is decremented. As described in the Croslin application, AUX3 (having alternate label AUX33, depending on which register bank is the working bank) is used to time a 60-millisecond interval starting with the detection of a blood pressure pulse; if the pulse has a duration shorter than 60 milliseconds, it is "discarded". AUX3 is initially set so that it is decremented down to 0 after 60 milliseconds. Once it reaches 0, the test at line 93 makes sure that it stays at 0. Thus when the pulse is over, a check can be made that it had a duration of at least 60 milliseconds simply by verifying that AUX3 is 0.

At line 95, data memory location AUX1 (register R5') is decremented and examined to see if it is 0. This register is used to time 100-millisecond intervals. If it is not 0, a jump is made to line 100. The timer flag was set at the end of the 800-microsecond timing cycle which caused the timer interrupt routine to be executed in the first place, and the JTF instruction resets it preparatory to another cycle of operation. A jump is made to the next line, TEXIT; the jump is not really required, but the JTF instruction is in order to reset the timer flag. Since the accumulator was originally saved at ASAV (register R7'), it is now restored, and lastly a return is made at line 102 to whatever instruction in the program would have been executed next had the timer interrupt not occurred. The RETR instruction is utilized at line 102 not only to return to the interrupted processing, but also to restore the program status word which is automatically saved in the stack provided for this purpose when the timer interrupt first occurs, and also to select bank 0 once again as the working register bank.

But if in line 95 AUX1 is decremented to 0, register R5' (AUX1) is loaded with a value of 125 at line 96. Since the value stored in AUX1 is decremented at line 95 once every 800 microseconds, it is apparent that it requires 100 milliseconds for AUX1 to be decremented from its initial count of 125 down to 0. By examining register R5', it is possible to determine when 100 milliseconds have elapsed, and this is actually done elsewhere in the program. Whenever 100 milliseconds have gone by, the contents of AUX2 are moved to the accumulator at line 97. As described in the Croslin application, this register (R') is initially loaded with a value of 100 (when the third pulse is detected) so that the number of pulses which occur in a 10-second interval can be counted. With the value of AUX2 moved to the accumulator at line 97, the accumulator is examined at line 98 to see if it is 0. If it is, a jump is made to line 100. If it is not 0, AUX2 is decremented at line 99. By continuously examining the value of AUX2 (done elsewhere in the program), it is possible to determine when 10 seconds have elapsed. There is no need to reset AUX2 to its initial value of 100, because there is only one 10-second timing interval during each patient measurement. (Also as will now be described, a 1-second delay can be generated by loading AUX2 with 10, rather than 100, it thus requiring only 10 cyclings of register AUX1, or one second, before AUX2 is decremented down to 0.)

Returning to the main program, after the timer is enabled and started at lines 119 and 120, a call is made at line 124 to the WT1SEC routine at line 734. This subroutine simply delays things for one second, and allows the machine to settle down and the power supplies to come up. (During this delay, the calibrate, "CAL", message is displayed as described above.) The accumulator is loaded with the value 10 at line 734, and register R0 is then loaded with the RAM address of register R6' (AUX22). At line 736, the accumulator contents are transferred to AUX22. (Location AUX22, when running with register bank 0, as the system is now, is the same as memory location AUX2 when the system is running with register bank 1 during timer interrupt processing.) Consequently, as just described above, register R6' is decremented once every 100 milliseconds, and it is decremented down to 0 after one second has elapsed. At line 737, the contents of register R6' are moved to the accumulator. The accumulator is tested at line 738 to see if it has been decremented down to 0; if not, line 737 is executed again. The system simply remains in a wait loop for one second until register R6' has been decre- down to 0. When it has been, line 739 causes a return to line 125.

The INS instruction at line 125 transmits an $\overline{\text{RD}}$ pulse (approximately 1 microsecond in width) through the inverter connected to the "initiate conversion" input of the analog-to-digital converter. When this input of the 8704 chip goes high, a new conversion cycle begins, and the BUSY output goes high. The BUSY output goes low when the conversion is complete. The results of the previous conversion appear at the bit 0–9 output pins of the converter while a new conversion is in progress; the data is changed only at the end of a conversion when the BUSY line goes low. During normal processing, the 8048 chip examines its $\overline{\text{INT}}$ input (the converter's BUSY output) to see if a new sample is available. If it is, an IN instruction is executed to read in the two bits of the sample at port 2, followed by execution of an INS instruction to read in the other eight bits of the sample appearing at the BUS inputs. The microprocessor is so fast that when it is ready for another sample, one is not yet available; the microprocessor just waits and examines its $\overline{\text{INT}}$ input to see if the A/D converter has pulsed its BUSY line low. Thus the rate at which pressure samples are taken (approximately once every 2.5 milliseconds) is determined by the speed of the A/D converter.

At line 125, an input instruction is executed, by which the $\overline{\text{RD}}$ output pin is pulsed low and the data appearing on the BUS lines are stored in the accumulator. The first data sample is not actually used (nor are its two most significant bits even read in) since it is meaningless—the converter was never told to initiate a conversion until now. The reason for executing the INS instruction at line 125 is to initiate a conversion; although the INS instruction causes a data sample to be loaded into the accumulator (which sample is not used), it also initiates a new conversion due to the connection of the $\overline{RD}$ pin through an inverter to the "initiate conversion" input of the converter.

The start sequence described thus far is shown on the flow chart of FIG. 10. The flow chart depicts only the more important operations, with the number to the left of each block in the flow chart identifying the first respective line number in the source program. The flow chart does not depict the manner in which a new message is displayed, nor how the display is refreshed following timer interrupts, inasmuch as these routines have been described in detail.

Reference Pressure, Initial Battery Check, and Factory Calibrate

The system of the invention does not actually measure the instantaneous absolute pressure in the cuff. Were it to do so, the machine would have to be calibrated to provide a predetermined pressure reading when the cuff is at atmospheric pressure. But atmospheric pressure varies from location to location, for example, it is lower at higher elevations. Consequently, the system is designed to operate on relative pressures, not absolute pressures. While the cuff is open to the atmosphere, the system takes a reference pressure reading, PREF. As all digital samples have ten bits, two bytes are required to store PREF. The first byte is stored in register R2' and the second byte is stored in register R3' (see line 41). With the V1 valve open, the system looks at successive pressure readings to see if they are changing. As long as they are changing, it is an indication that the cuff was not originally at atmospheric pressure and air is either flowing into or out of it. PREF is constantly up-dated. As soon as the pressure readings cease to change, the latest up-dated PREF value is the final reference pressure. All other pressure readings are taken to be the difference between the actual sample outputted by the converter and the reference pressure. Thus no matter what the atmospheric pressure, each pressure sample which is actually processed is a pressure relative to atmospheric pressure. (PREF does not equal the atmospheric pressure due to the offset introduced by amplifier B of chip IC3 on FIG. 4. There is no need to know the atmospheric pressure, just the measured pressure when the cuff is at atmospheric pressure—since all samples processed are only relative values.)

During factory calibration, it is only necessary to insure that for some test pressures which exceed atmospheric pressure by a known amount, the readings taken represent the differences, and not the absolute pressures. There are several potentiometer adjustments which may be made to insure that when the cuff is open to the atmospere the measured (relative) pressure is zero, and when a pressure of known value is in the cuff, the measured (relative) pressure is equal to the actual pressure minus atmospheric pressure.

After waiting for one second (line 124) and initiating a conversion (line 125), at line 126 a call is made to the REFP subroutine at line 914. A call is immediately made to the READPR subroutine at line 476. As described above, while a conversion is in progress, the BUSY output of the converter is high. This output is coupled to the $\overline{INT}$ input of the 8048 chip. The external interrupt is never enabled, and the $\overline{INT}$ input to the chip is tested to determine when a new sample is available. The JNI instruction at line 476 causes a jump to the GETP routine at line 478 if the $\overline{INT}$ input is low. Otherwise, the JMP instruction at line 477 simply causes the processor to remain in a wait loop, going back to the JNI instruction until the $\overline{INT}$ input goes low.

It will be noted that in FIG. 5 bits 0–7 of the converter are applied to the BUS inputs, while bits 8 and 9 are applied to bits 0 and 1 of port 2. It is these two latter bits which are first operated upon. The IN instruction at line 478 loads the accumulator with the bit values at port 2. (Ports 1 and 2 serve as both outputs and inputs; it is this property which allows latched outputs to be read in, as described above, and also allows input signals to override latched outputs if they are high. The original reset command causes the microprocessor to latch all of its port outputs high.) At line 479, the accumulator contents are ANDed with the HEX digits 03, thus clearing all digits except the two least significant which contain bits 8 and 9 of the converter output. The accumulator contents are then stored at AEX (register R2). The other eight bits are then read upon execution of the INS instruction, the eight least significant bits of the present sample appearing in the accumulator. (Execution of the INS instruction also starts another conversion.) Finally, the address of the PREF location in data memory is stored in register R0, and a return is made to line 915.

At this time a call is made to the DST subroutine at line 724. Since register R0 contains the address of location PREF, the least significant byte of the sample, now in the accumulator, is stored in location PREF. The XCH instruction then exchanges the least and most significant bytes, the most significant byte having been previously stored in location AEX at line 480. Register R0 is then incremented to point to the data memory location following PREF, and the most significant byte is stored at this location. Finally, the accumulator and AEX register contents are interchanged (to leave the two registers with their original contents), and register R0 is similarly decremented to restore its original contents. At line 730, a return is made to line 916, from which a return is made to line 130.

This operation is shown by the first block in the flow chart of FIG. 11, "get reference pressure". As will be described below, the reference pressure will be changed if the cuff is not originally at atmospheric pressure. But before this is done, the battery is checked to see if its potential is high enough for proper system operation.

The ROM program actually contains a sequence for testing whether the battery potential is both greater than 9.8 volts and less than 9.4 volts. Despite the fact that this is a physical impossibility, if this test condition is passed, a branch is made to a special subroutine. This special subroutine is one which allows the unit to be calibrated in the factory to provide accurate pressure readings. At the factory, a test chip is placed on the unit which forces the "impossible" test to be passed. A branch is then made to a "factory calibrate mode" routine which is only executed in the factory, and never executed when the unit is actually used in its normal mode. The ROM is actually shipped with a routine which is never executed during normal use. The routine is included in the program only to facilitate factory calibration. By including the routine in the program, however, factory calibration is greatly simplified.

Referring to FIGS. 3–5, the output of comparator A of chip IC10 is extended to the T1 input test pin of the microprocessor. Whenever the battery potential exceeds 9.8 volts, the output of the comparator is high; otherwise it is low. Similarly, the output of comparator B of chip IC10 is extended to bit 2 of port 2. During normal operation of the machine, the output of the comparator is high whenever the battery potential is greater than 9.4 volts, and it is low whenever the battery potential is less than 9.4 volts. It will be noted, however, that resistor R9 on FIG. 4, connected to the positive input of the comparator, can be connected to ground via a test chip in the factory. If the test clip connects the resistor to ground, the output of the comparator B goes low even if the battery potential exceeds 9.4 volts. Thus a technician in the factory can force the "impossible" test to be passed—the battery potential exceeds 9.8 volts as reflected at the T1 input of the processor, and the battery potential is below 9.4 volts as reflected at bit 2 of port 2.

At line 130, the port 2 input bits are stored in the accumulator. The JB2 instruction tests bit 2 of the accumulator and thus in effect it examines the 9.4-volt test line. If the bit value is a 1, indicating that the battery potential exceeds 9.4 volts, the unit is in actual use by a patient and is not being factory calibrated. A jump is made to the DELCHK routine at line 153. As will be described below, starting here a check is made whether the battery is only partially charged (greater than 9.4 volts but less than 9.8 volts, allowing up to 25 addtional measurements to be made before the battery goes "dead"). The DELCHK routine also makes sure that the cuff pressure is at atmospheric pressure before the final reference pressure (PREF) reading is assumed to be valid.

But if the test at line 131 indicates that the battery potential is below 9.4 volts, the test at line 132 is executed. The T1 input bit is examined; if it is low, indicating that the unit is not being calibrated in the factory (at which time the battery is fully charged), a jump is made to the DELCHK routine which then begins all over again to examine the state of the battery and to flash an appropriate message if necessary. But if the test at line 132 indicates that the battery potential exceeds 9.8 volts, and since the previous test which resulted in line 132 being executed in the first place indicated that the battery potential is also below 9.4 volts, it is an indication that the unit is being calibrated in the factory and the program advances to line 133. During factory calibration (which should not be confused with the automatic calibration which occurs every time the unit is turned on, or the reset key is depressed, i.e., the DELCHK routine), the valve within the unit which vents the cuff to the atmosphere (inside the housing) is closed. This allows the unit to be calibrated by maintaining known pressures in the cuff and insuring that the correct pressure values are displayed, as will be described below. When the system is first reset, to start a measurement sequence, the output ports are automatically latched high. Thus initially the valve is open because bit 3 of port 2 is high. To close the valve it is necessary to force this bit output low. The ANL instruction at line 133 closes the valve. Whatever the output latched at port 2, the ANL instruction clears bit 3. The low potential at bit 3 of port 2 (FIG. 5) which is now latched, is then inverted once again by four inverter connected in parallel (to provide sufficient drive current for the valve coil, when needed). One end of the coil is connected to 9.6 volts, and the other is now grounded. The valve is normally open, but with a 0 at bit 3 of port 2, coil current flows and the valve closes.

At line 137, a call is made to the DPRESS subroutine at line 499. The instruction at line 499 loads the accumulator with the relative address in page 3 of the first byte (two characters) in the "PRESS" message. The program then proceeds with the DALPHA routine described above which actually results in the display of the selected message. As the unit measures the pressures in the cuff applied by the factory technician, he is informed that cuff pressure readings are being displayed. A return is then made to line 138. The three-digit pressure values are displayed in the last three character positions of the display. Just in case a minus sign is required, it is now displayed. (It is soon erased, if the pressure is not negative.) The address of the fourth from the last location in the display table is loaded into register R1, and at line 139 the HEX digits BF are stored at this location. These HEX digits cause a minus sign to be displayed when applied (through inverters) to the display segment drivers. The minus sign is displayed automatically, as every character or digit is when its respective segments are loaded into one of the twelve locations in the display table.

At line 140, a call is made to the READP subroutine at line 487. This subroutine simply calls the READPR subroutine (line 476) described above, which reads the latest pressure sample into AEX and the accumulator, and then stores the address of location PREF in register R0.

After lines 476-483 are executed, a return is made to line 491, PDIF. The sample value is now stored in PTMP and PTMP+1. At line 491, address PTMP is stored in register R0. The call to the DST subroutine (line 724) causes the sample value in AEX and the accumulator to be stored in two locations, the first of which is in register R0. The address of the first location containing the reference pressure, PREF, is then loaded into register R1, and a call is made to the DMINV subroutine at line 612.

This subroutine, between lines 612 and 632 is straightforward and will not be described in detail. The double-precision value pointed to by register R1 is subtracted from the double-precision value pointed to by register R0; no stored register (R0 and R1) values change, and the purpose of the subroutine is to set the carry flag and to store the difference in the accumulator and in AEX (with the least significant byte in the accumulator). In the present case, the carry flag is set if the difference between the just taken pressure value and the reference pressure value is zero or positive.

Lines 601-610 should be understood. When the DMINV subroutine is executed, the data (Y) pointed to by register R1 is subtracted from the data (X) pointed to by register R0. The binary difference appears in AEX and the accumulator. As for the carry bit, it is set to 1 if $X \geq Y$; and it is set to 0 only if $Y > X$. A call to DMINC (line 618) provides a similar result. In this case, instead of Y being data pointed to by register R1, the data in the accumulator and AEX are used when forming the difference $X - Y$. The DADDC subroutine (line 625) is similar to the DMINC subroutine but involves addition, not subtraction.

When a return is made to line 495, a jump is made to the DST subroutine at line 724. Since register R0 contains PTMP, the difference represented by the accumulator and AEX is stored in PTMP and PTMP+1. A return is then made to line 141.

The method of operation described thus far is as follows. PREF and PREF+1 have the reference pressure—which is atmospheric—as controlled by line 126. A sample value is then taken and temporarily stored at PTMP and PTMP+1. The reference pressure is then subtracted from this value, and the difference stored in PTMP and PTMP+1. It is the difference which is displayed, and the difference is the actual sample value less the reference pressure.

At line 141, flag F0 is cleared. This flag is cleared for (PTMP-PREF) pressure values which are positive, and it is assumed that the value is positive. If it is, the carry bit was set by the DMINV subroutine and at line 142 a jump is made to line 147 which actually controls the display of the pressure value.

If the pressure is negative, the program advances to line 143. First, flag F0 is set by complementing it, to indicate a negative pressure. A call is then made to the DADDC subroutine at line 625. The double-precision value pointed to by register R0 is added to the double-precision value contained in AEX and the accumulator. Since register R0 points to PTMP, and locations PTMP and PTMP+1 contain the difference pressure still stored in AEX and the accumulator, twice the difference (a negative value) is formed.

At line 145, the DMINC subroutine is called. This subroutine forms the difference between the double-precision value pointed to by register R0 and the contents of AEX and the accumulator. In the present case, the net result is that the original negative pressure value is negated. The call to DST at line 146 then causes the negated pressure value (now positive) to be stored in PTMP and PTMP+1.

At line 147, a call is made to the DSPRES subroutine at line 514 in order to display a pressure value. The system resolution is 0.5 mm Hg, that is, if a pressure sample, minus the reference pressure, is X, then the stored value is 2X. To display the contents of PTMP and PTMP+1, the value must be halved, and then converted to BCD form in order to access digit segment bytes.

After loading register R0 with the PTMP address, at line 515 the BINBCD subroutine is called (line 639). Digits are displayed in groups of three; location BCD0 must contain a code representing a blank (BH) followed by the code of the most significant BCD digit to be displayed, and location BCD1 must contain the two least significant BCD digit codes to be displayed. Address BCD0 is first loaded into register R1 at line 639.

Registers R0 and R1 are then incremented so that they point respectively to locations PTMP+1 and BCD1. The carry flag is cleared (preparatory to the ensuing operations), and the byte pointed to by register R0 (the most significant PTMP pressure byte) is placed in the accumulator, shifted one bit position to the right through the carry flag, and then stored in the location BCD1 (which follows location BCD0 in the data memory). Registers R0 and R1 are then decremented to point to PTMP and BCD0, and at line 651 PTMP is loaded into the accumulator. The right shift starting at line 652 causes any bit shifted to the right from the earlier shift of the most significant (PTMP+1) pressure byte to be shifted into the most significant bit position of the least significant byte (PTMP). The net result is that the 2-byte PTMP pressure value is halved by shifting it to the right, and it is transferred from PTMP and PTMP+1 to BCD0 and BCD1. The resolution of the system is 0.5 mm Hg, and the shifting procedure provides the actual pressure (in binary form).

The maximum sample value of 10 bits is 1024. When halved, this gives a maximum value of 512. Thus three BCD digits must be formed. The binary to BCD conversion method between lines 657 and 681 is well known. First, increments of 100 are subtracted from the 9-bit binary value until the result would be negative. The number of increments which leave a positive value (under 100) is the first BCD digit, stored in the least significant nibble of BCD0. (The most significant nibble is loaded with the HEX code representing a blank. The least significant nibble is loaded with 0 if the pressure value being operated upon is less than 100). In a similar manner, by subtracting increments of 10 from successive remainders until the final remainder is between 0 and 9, the tens digit can be determined and stored in the most significant nibble of BCD1. Finally, the remainder—the units digit—is stored in the least significant nibble of BCD1. A return is then made to line 516.

As described above, the DISP routine stores any message, or message part, in the display table. The set-up for calling the routine is as follows: (1) AEX must represent the number of characters (alphabet or digit) to be placed in the display table; since two characters are processed for each message or double-BCD byte, and AEX is decremented only after bytes are processed, AEX must have a value of 1 to process four BCD digits. (2) Register R0 must contain either the first message relative address, or for digits the value BCD0. (3) Register R1 must contain the position of the first character to be placed in the display table, in this case DTBL+8, the fourth position from the end. (4) FLag F1 must be cleared to display alphabet character messages, and it must be set to 1 to display digits.

When the system returns to line 516 the address DTBL+8 is loaded into the accumulator. The DBCD routine at line 523 then establishes the four set-up conditions. Registers AEX, R0 and R1 are loaded as required in lines 523-525, and in lines 526 and 527 flag F1 is set. At line 528 a jump is made to the DISP subroutine at line 533. The rest is automatic; the digit segment bytes are loaded in the display table and the display is updated automatically during the timer interrupt routine.

After the message is up-dated, a return is made to line 148. There are actually four digit segment bytes which are loaded into the display table but the first, at location DTBL+8, represents a blank. If the pressure value is negative, however, a minus sign should be displayed at the display position corresponding to display table address DTBL+8. A minus sign segment byte was originally stored at address DTBL+8 at lines 138 and 139, but it has been erased. A test is made at line 148 to see if the pressure is negative. If flag F0 is set, indicating a negative pressure, a jump is made to line 138 so that the minus sign is displayed. Otherwise, a jump is made at line 149 to line 140 where the process repeats itself but without a minus sign being substituted for the blank.

It is thus apparent that during factory calibration, whatever pressure the technician applies to the cuff appears on the display. Two potentiometers (coarse and fine) are provided as an offset control (FIG. 4). These potentiometers are adjusted so that a pressure of 0 is displayed when the applied pressure equals atmospheric pressure (cuff open to atmosphere, i.e., bulb removed). The cuff tubing may then be connected to an accurate manometer and to a bulb without a bleed hole. When the bulb is pumped to apply a pressure of 200 mm Hg (as registered on the manometer) to the cuff, for example, the two gain potentiometers (coarse and fine) are adjusted until a reading of 200 is obtained. With the system calibrated properly for relative pressures at 50 mm increments from 0 to 300 mm, it can be assumed that it will operate properly over the entire range. The unit remains in the factory calibrate mode and simply continues to display the cuff pressure. To exit the loop, the technician presses the reset button, if desired, in order to restart the machine and further test it.

As described above, the program jumps to line 153 when the unit is actually being used by a patient, at which time the battery is checked and the reference pressure is changed if necessary. A call is first made to the BDEAD routine at line 693. The IN ad JB2 instructions test bit 2 of port 2. If this bit is a 1, indicating that the battery potential is above 9.4 volts, a return is made to line 154. But if the bit value is a 0, indicating that the battery is dead, the instruction at line 695 is executed. The accumulator is loaded with the relative address in page 3 which contains the "CH dC" message, i.e., the unit cannot be used because the battery needs recharging. A call is then made to the BLINK subroutine at line 685. A call is immediately made to the BLINK1 subroutine at line 687, which in turn calls the DALPHA subroutine to control display of the message. The accumulator is then loaded with the number 3 and a jump is made to the WAIT subroutine at line 735. Referring to line 734, it will be recalled that when the accumulator is loaded with the number 10, a 1-second delay is generated. With the accumulator now loaded with the number 3 and the jump being made to line 735, a 0.3-second delay is generated. When the RET instruction is executed at line 739, a return is made to line 686. The accumulator is now loaded with the relative address in page 3 of the location containing the first two characters of a "blank" message, and a call is then made to the DALPHA subroutine. After the return from this subroutine and another execution of the WAIT (0.3-second) subroutine, a return is made to line 697, which immediately causes a jump to the line (695) which started the whole process. In this way, the "CH dC" message is displayed for 0.3 seconds, following which the display is blanked for 0.3 seconds. The cycle is self-repeating, and the system remains in an endless loop with no measurements being possible. The user must recharge the battery in order to further utilize the unit.

If the battery is not dead, the call at line 154 controls a delay of one second to allow the cuff pressure to settle down to atmospheric pressure. (The valve is still open, as it has been since reset; line 133 is executed to close the valve only during factory calibration.) Then the reference pressure stored in PREF and PREF+1 (line 126) is corrected if necessary; this is accomplished before the system checks whether the battery potential is above 9.8 volts or below it (but above 9.4 volts—which must be the case if line 155 is reached).

At line 155 the pressure is read. The called READP subroutine at line 487 calls the READPR subroutine which stores the pressure sample in PTMP and PTMP+1, with register R0 pointing to PTMP. The PDIF routine at line 491 then replaces the pressure sample in PTMP and PTMP+1 by the relative pressure (sample value less reference value). When a return is made to line 156, the address of PLAST is loaded into register R1. A call is then made to the DMOVE subroutine at line 902. This subroutine (lines 902-910) causes the contents of the 2-byte location pointed to by register R0 to be loaded into the 2-byte location pointed to by register R1, with no change in the values stored in the pointer registers. In this case, the sample value just taken and stored in PTMP and PTMP+1 is loaded into PLAST and PLAST+1.

At line 158, another pressure sample is taken and loaded into PTMP and PTMP+1. A test is now performed to see if the two samples differ. Register R1 is made to point to PLAST; register R0 still points to PTMP. Thus the call to DMINV forms the difference between the two sample values. If the difference is zero or positive, the carry flag is set, and at line 161 a jump is made to line 164. Otherwise, the difference in the accumulator (the difference is small so the two most significant bits in AEX can be ignored) is negated by the CPL and INC instructions. In either case, the test at lines 164 and 165 is executed, working with a positive value contained in the accumulator.

The test is simply to see if the two samples were the same to within 1 mm Hg. The accumulator contains a positive value no matter what the sign of the actual difference. A 1 mm Hg difference is represented by a value of 2 since each sample value is twice the actual pressure. Therefore, at line 164, −2 is added to the accumulator. In HEX notation, and using 2's complement arithmetic (since that is what the assembler does), −2 is translated to FEH. If the accumulator contains a value of 0 or 1 (00H or 01H), corresponding to a pressure difference of 0 or 0.5 mm Hg, the addition of −2 to the accumulator gives a result of FEH, or FFH, and the carry bit is not set. The cuff pressure therefore changed by less than 1 mm Hg between the last two samples, it is assumed that the cuff pressure is at atmospheric pressure, the reference pressure value (at PREF and PREF+1) is correct, and the JC instructon at line 165 causes processing to proceed at line 170. But if the difference exceeds 1 mm Hg, the cuff pressure is not yet at atmospheric pressure, the ADD instruction at line 164 sets the carry flag, and the JC instruction at line 165 causes a branch to be made to line 126, at which time a new reference pressure reading is taken. Because the valve is open, ultimately the cuff pressure will be at atmospheric pressure, there will be less than a 1 mm Hg change in successive pressure samples, and processing will proceed to line 170.

FIG. 11 is the flow chart depicting in broad outline the processing involved during the initial battery check, the factory calibration procedure, and the derivation of reference pressure.

Subsequent Blood Pressure Processing

The remainder of the instrument cycling is described in the Croslin application. Only a brief summary of the operation will be given herein because the steps in the Croslin methodology are not pertinent to the present invention which is being claimed.

The operator is informed to press the recall/cuff key by one of two messages. The usual message is "CUFF". However, if the battery potential is low, but not that low so that a measurement may not be taken, the message which is displayed is "LO dC". The latter message means the same thing as "CUFF", but it further informs the operator that the battery should be recharged.

After the recall/cuff key is operated, the message "OCCLUDE" is displayed; this is an indication to the operator that he should start pumping the bulb. As the bulb is pumped, the "PrESS" (pressure) message is displayed, together with the numerical value of the cuff pressure in accordance with the most recent sample. After the operator stops pumping the bulb, and as the cuff pressure starts to bleed down, the system checks that no blood pressure pulses appear during a 2.5-second time interval. If any pulses do appear, the "LO OCC PrESS" message is displayed to indicate that the occluding pressure is too low, and that the operator should pump up the bulb again. But if no pulses are detected for 2.5 seconds, the system proceeds to analyze successive pressure samples and to derive values of systolic pressure, diastolic pressure, and heart rate.

At the end of the measurement cycle, the three values are displayed for ten seconds. To conserve power, the display is then blanked, but the values may be recalled by pressing the recall/cuff key. While the display is blanked, the pulse light is turned on to inform the operator that the display can be recalled.

The complete listing is described in the Croslin application. That description includes a conditional assembly (which requires TEST to be set equal to TRUE in line 11) for producing code which results in the display of the height of each detected blood pressure pulse in the form of a single HEX digit. While this display is not made available to the user, it is of value in the design of an instrument.

It will be apparent that much of the above description pertains to the operation of the instrument in the normal mode as well as in the factory-adjustment mode. That is because there is an overlap in the code which controls the two sequences, and it is also necessary to understand the normal use of the two battery test signals in order to appreciate how they control a branch to the factory-adjustment mode when a technician forces inconsistent test conditions. Despite the fact that there are no available test inputs which could be used exclusively to control a ranch, the test inputs which are used for other purposes can be made to control the branch simply by forcing them to represent an overall system state which cannot arise during normal use of the instrument.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

What I claim is:

1. A microprocessor-controlled apparatus comprising microprocessor/firmware means for controlling a normal mode of operation and a factory-adjustment mode of operation, said apparatus sequencing in the two modes under control of different portions of firmware having a part in common, means for developing at least one signal indicative of the state of the apparatus for testing by said microprocessor/firmware means to control at least one firmware branch, and control means for placing the apparatus in a predetermined state in the factory so that after execution of said common firmware a branch is made to that portion of the firmware which controls sequencing of the apparatus in the factory-adjustment mode, the apparatus not entering said predetermined state during sequencing in the normal mode.

2. A microprocessor-controlled apparatus in accordance with claim 1 wherein said signal developing means includes means for developing at least two signals which represent compatible test conditions during normal operation of the apparatus, and said control means causes said at least two signals to represent incompatible test conditions.

3. A microprocessor-controlled apparatus in accordance with claim 2 wherein said at least two signals represent battery levels, and said incompatible test conditions represent battery levels both above and below an intermediate level.

4. A microprocessor-controlled apparatus in accordance with claim 3 wherein the normal mode the apparatus measures blood pressure, and in the factory-adjustment mode the apparatus provides measurements of known pressures so that it can be calibrated.

5. A microprocessor-controlled apparatus in accordance with claim 2 wherein in the normal mode the apparatus measures blood pressure, and in the factory-adjustment mode the apparatus provides measurements of known pressures so that it can be calibrated.

6. A microprocessor-controlled apparatus in accordance with claim 1 wherein in the normal mode the apparatus measures blood pressure, and in the factory-adjustment mode the apparatus provides measurements of known pressures so that it can be calibrated.

7. A microprocessor-controlled apparatus comprising microprocessor/firmware means for controlling a normal mode of operation in which the apparatus functions in its intended end use, and an adjustment mode of operation in which the apparatus functions in a manner facilitating changes being made thereto which affect the normal mode of operation, said apparatus sequencing in the two modes under control of different portions of firmware; means for developing at least one signal indicative of the state of the apparatus for testing by said microprocessor/firmware means to control at least one firmware branch; and control means for placing the apparatus in a predetermined state so that a branch is made to that portion of the firmware which controls sequencing of the apparatus in the adjustment mode, the apparatus not entering said predetermined state during sequencing in the normal mode.

8. A microprocessor-controlled apparatus in accordance with claim 7 wherein said signal developing means includes means for developing at least two signals which represent compatible test conditions during normal operation of the apparatus, and said control means causes said at least two signals to represent incompatible test conditions.

9. A microprocessor-controlled apparatus in accordance with claim 8 wherein said at least two signals represent battery levels, and said incompatible test conditions represent battery levels both above and below an intermediate level.

10. A microprocessor-controlled apparatus in accordance with claim 9 wherein in the normal mode the apparatus measures blood pressure, and in the adjustment mode the apparatus provides measurements of known pressures so that it can be calibrated.

11. A microprocessor-controlled apparatus in accordance with claim 8 wherein in the normal mode the apparatus measures blood pressure, and in the adjustment mode the apparatus provides measurements of known pressures so that it can be calibrated.

12. A microprocessor-controlled apparatus in accordance with claim 7 wherein in the normal mode the apparatus measures blood pressure, and in the adjustment mode the apparatus provides measurements of known pressures so that it can be calibrated.

13. A method for operating a microprocessor-controlled apparatus, the apparatus having microprocessor/firmware means for controlling a normal mode of operation and a factory-adjustment mode of operation, said apparatus sequencing in the two modes under control of different portions of firmware having a part in common, and means for developing at least one signal indicative of the state of the apparatus for testing by said microprocessor/firmware means to control at least one firmware branch; comprising the steps of (a) placing the apparatus in a predetermined state in the factory so that after execution of said common firmware a branch is made to that portion of the firmware which controls sequencing of the apparatus in the factory-adjustment mode, the apparatus not entering said predetermined state during sequencing in the normal mode; and (b) adjusting the apparatus as it sequences in the factory-adjustment mode.

14. A method in accordance with claim 13 wherein said signal developing means includes means for developing at least two signals which represent compatible test conditions during normal operation of the apparatus, and in step (a) said at least two signals are caused to represent incompatible test conditions.

15. A method in accordance with claim 14 wherein said at least two signals represent battery levels, and said incompatible test conditions represent battery levels both above and below an intermediate level.

16. A method in accordance with claim 15 wherein in the normal mode the apparatus measures blood pressure, and in the factory-adjustment mode the apparatus provides measurements of known pressures so that it can be calibrated, known pressures being applied in step (b) as the apparatus is calibrated.

17. A method in accordance with claim 14 wherein in the normal mode the apparatus measures blood pressure, and in the factory-adjustment mode the apparatus provides measurements of known pressures so that it can be calibrated, known pressures being applied in step (b) as the apparatus is calibrated.

18. A method in accordance with claim 13 wherein in the normal mode the apparatus measures blood pressure, and in the factory-adjustment mode the apparatus provides measurements of known pressures so that it can be calibrated, known pressures being applied in step (b) as the apparatus is calibrated.

19. A method for operating a microprocessor-controlled apparatus, the apparatus having microprocessor/firmware means for controlling a normal mode of operation in which the apparatus functions in its intended end use, and an adjustment mode of operation in which the apparatus functions in a manner facilitating changes being made thereto which affect the normal mode of operation, said apparatus sequencing in the two modes under control of different portions of firmware; and means for developing at least one signal indicative of the state of the apparatus for testing by said microprocessor/firmware means to control at least one firmware branch; comprising the steps of (a) placing the apparatus in a predetermined state so that a branch is made to that portion of the firmware which controls sequencing of the apparatus in the adjustment mode, the apparatus not entering said predetermined state during sequencing in the normal mode; and (b) adjusting the apparatus as it sequences in the adjustment mode.

20. A method in accordance with claim 19 wherein said signal developing means includes means for developing at least two signals which represent compatible test conditions during normal operation of the apparatus, and in step (a) said at least two signals are caused to represent incompatible test conditions.

21. A microprocessor-controlled apparatus in accordance with claim 20 wherein said at least two signals represent battery levels, and said incompatible test conditions represent battery levels both above and below an intermediate level.

22. A method in accordance with claim 21 wherein in the normal mode the apparatus measures blood pressure, and in the adjustment mode the apparatus provides measurements of known pressures so that it can be calibrated, known pressures being applied in step (b) as the apparatus is calibrated.

23. A method in accordance with claim 20 wherein in the normal mode the apparatus measures blood pressure, and in the adjustment mode the apparatus provides measurements of known pressures so that it can be calibrated, known pressures being applied in step (b) as the apparatus is calibrated.

24. A method in accordance with claim 19 wherein in the normal mode the apparatus measures blood pressure, and in the adjustment mode the apparatus provides measurements of known pressures so that it can be calibrated, known pressures being applied in step (b) as the apparatus is calibrated.

* * * * *